US011149250B2

(12) United States Patent
Douvaras et al.

(10) Patent No.: US 11,149,250 B2
(45) Date of Patent: Oct. 19, 2021

(54) MICROGLIA DERIVED FROM PLURIPOTENT STEM CELLS AND METHODS OF MAKING AND USING THE SAME

(71) Applicant: NEW YORK STEM CELL FOUNDATION, INC., New York, NY (US)

(72) Inventors: Panagiotis Douvaras, New York, NY (US); Scott Noggle, Long Island City, NY (US); Stephen Chang, New York, NY (US); Valentina Fossati, New York, NY (US)

(73) Assignee: New York Stem Cell Foundation, Inc., New York, NY (US)

( * ) Notice: Subject to any disclaimer, the term of this patent is extended or adjusted under 35 U.S.C. 154(b) by 0 days.

(21) Appl. No.: 15/449,519

(22) Filed: Mar. 3, 2017

(65) Prior Publication Data

US 2017/0253856 A1 Sep. 7, 2017

Related U.S. Application Data

(60) Provisional application No. 62/410,645, filed on Oct. 20, 2016, provisional application No. 62/303,301, filed on Mar. 3, 2016.

(51) Int. Cl.
| | |
|---|---|
| *C12N 5/079* | (2010.01) |
| *C12N 5/0735* | (2010.01) |
| *A61K 35/30* | (2015.01) |
| *G01N 33/50* | (2006.01) |

(52) U.S. Cl.
CPC ............ *C12N 5/0622* (2013.01); *A61K 35/30* (2013.01); *C12N 5/0606* (2013.01); *C12N 5/0618* (2013.01); *G01N 33/5058* (2013.01); *C12N 2500/90* (2013.01); *C12N 2501/155* (2013.01); *C12N 2501/22* (2013.01); *C12N 2501/2334* (2013.01); *C12N 2506/45* (2013.01)

(58) Field of Classification Search
CPC ............. A61K 35/30; C12N 5/060606; C12N 5/0622; C12N 5/0623; C12N 5/0634; C12N 5/0692
See application file for complete search history.

(56) References Cited

U.S. PATENT DOCUMENTS

| | | |
|---|---|---|
| 2012/0107898 A1 | 5/2012 | Neumann et al. |
| 2016/0186137 A1 | 6/2016 | Thomas et al. |

FOREIGN PATENT DOCUMENTS

WO   WO 2013/116307 A1   8/2013

OTHER PUBLICATIONS

Stemcell Technologies, www.stemcell.com/products, TeSR medium (2019).*
Cope, EM: "*Directed differentiation of human embryonic stem cells to microglial-like cells*"; Doctoral Thesis, Cardiff University [online]. 2014 [Retrieved on Apr. 28, 2017]. Retrieved from the Internet: <URL: http://orca.cf.ac.uk/72156/>; p. 43.
International Search Report dated May 30, 2017, regarding PCT/US2017/020709.
Lin, H. et al.: "*Discovery of a Cytokine and Its Receptor by Functional Screening of the Extracellular Proteome*"; Science, May 9, 2008, vol. 320, No. 5877; pp. 807-811.
Pre, D. et al.: "*A Time Course Analysis of the Electrophysiological Properties of Neurons Differentiated from Human Induced Pluripotent Stem Cells iPSCs*";. PLOS One, Jul. 29, 2014, vol. 9, No. 7; e103418; p. 2.
Qi, X. et al.: "*BMP4 supports self-renewal of embryonic stem cells by inhibiting mitogen-activated protein kinase pathways*"; Proceedings of the National Academy of Sciences of the U.S.A., Apr. 20, 2004, vol. 101, No. 16; pp. 6027-6032.
Etemad, Samar et al.: "*A novel human model: Characterization of human monocyte-derived microglia*"; J. Neuroscience Methods, vol. 209, No. 1. May 22, 2012, pp. 79-89, XP028431611, ISSN: 0165-0270, DOI: 10.1016/J.JNEUMETH.2012.05.025, [retrieved on May 30, 2012].
Extended European Search Report dated Jul. 24, 2019, regarding EP 17 76 0917.
Ohgidani, Masahiro et al.: "*Direct induction of ramified microglia-like cells from human monocytes: Dynamic microglial dysfunction in Nasu-Hakola disease*"; Scientific Reports, vol. 4, May 14, 2014, pp. 1-7, XP055356890, DOI: 10.1038/srep04957.
Yanagimachi, Masakatsu D. et al.: "*Robust and Highly-Efficient Differentiation of Functional Monocytic Cells from Human Pluripotent Stem Cells under Serum- and Feeder Cell-Free Conditions*"; PLOS One, vol. 8, No. 4, Jan. 1, 2013, p. e59243, XP055158109, DOI: 10.1371/journal.pone.0059243.
Aarum, J., et al., "Migration and differentiation of neural precursor cells can be directed by microglia", Proceedings of the National Academy of Sciences of the United States of America 100, (2003), p. 15983-15988.
Ajami, B., et al., "Local self-renewal can sustain CNS microglia maintenance and function throughout adult life", Nature Neuroscience 10, (2007), pp. 1538-1543.
Bennett, M.L., et al., "New tools for studying microglia in the mouse and human CNS", Proceedings of the National Academy of Sciences of the United States of America 113, (2016), pp. 738-1746.
Beutner, C., et al., "Generation of microglial cells from mouse embryonic stem cells", Nature protocols 5, (2010), pp. 1481-1494.
Butovsky, O., et al., "Identification of a unique TGF- Dependent molecular and functional sigrtature in microglia", Nature neuroscience, 17(1), (2014), pp. 131-143.

(Continued)

*Primary Examiner* — Robert C Hayes
(74) *Attorney, Agent, or Firm* — Goodwin Procter LLP

(57) ABSTRACT

The present invention provides methods and compositions for the generation of microglial progenitor cells and microglial cells from pluripotent stem cells, such as embryonic stem cells and induced pluripotent stem cells. The present invention also provides cells produced using such methods, and both methods of treatment and methods of drug screening that use such cells. Also provided are various tissue culture media, tissue culture media supplements, and kits useful for the generation of human microglial progenitor cells and human microglial cells.

17 Claims, 25 Drawing Sheets

(56) References Cited

OTHER PUBLICATIONS

Colton, C.A., et al., Production of superoxide anions by a CNS macrophage, the microglia. PEBS letters, vol. 223, (1987), pp. 284-288.

Davalos, D., et al., "ATP mediates rapid microglial response to local brain injury in vivo", Nature neuroscience 8, (2005), pp. 752-758.

Douvaras, P., et al., "Efficient generation of myelinating oligodendrocytes from primary progressive multiple sclerosis patients by induced pluripotent stem cells", Stem cell reports 3, (2014), pp. 250-259.

Enomoto, R., et al., "Proposal for a new evaluation of phagocytosis using different sizes of fluorescent polystyrene microspheres", Advances in Biological Chemistry 03, (2013), pp. 556-563.

Fenn, A.M., et al., "Lipopolysaccharide-induced interleukin (IL)-4 receptor-a expression and corresponding sensitivity to the M2 promoting effects of IL-4 are impaired in microglia of aged mice", Brain, behavior, and immunity 26, (2012), pp. 766-777.

Ginhoux, F., et al., "Fate mapping analysis reveals that adult microglia derive from primitive macrophages", Science 330, (2010), pp. 841-845.

Hanisch, U.K., et al., "Microglia: active sensor and versatile effector cells in the normal and pathologic brain", Nature neuroscience 10, (2007), pp. 1387-1394.

Haynes, S.E., et al., "The P2Yi2 receptor regulates microglial activation by extracellular nucleotides", Nature neuroscience 9, (2006), pp. 1512-1519.

Hickman, S.E., et al., "The microglial sensome revealed by direct RNA sequencing", Nature neuroscience 16, (2013), pp. 1896-1905.

Japanese Patent Office, Notice of Reasons for Rejections, JP App. No. 2018-546540 (Mar. 29, 2021), 5 pages.

Kierdorf, K., et al. "Microglia emerge from erythromyelciid precursors via Pu.1- and Irf8-dependent pathways", Nature neuroscience 16 (2013), pp. 273-280.

Liao, Y., et al. "FeatureCounts: an efficient general purpose program for assigning sequence reads to genomic features", Bioininforrnatics 30, (2014), pp. 923-930.

Luheshi, N.M., et al., "Interleukin-1 a expression precedes IL-1 B after ischemic brain injury and is localised to areas of focal neuronal loss and penumbral tissues", Journal of neuroinflammation 8, 186 (2011), pp. 1-5.

Moore, C.S., et al., "P2YI2 expression and function in alternatively activated human microglia", A.A. Neurology, neuroimmunology & neuroinflammation 2: e80 (2015), pp. 1-10.

Muffat, J., et al., "Efficient derivation of microglia-like cells from human pluripotent stem cells", Nature medicine 22, (2016), pp. 1358-1367.

Napoli, 1., et al., "Microglial clearance function in health and disease", Neuroscience 158 (2009), pp. 1030-1038.

Napoli, I., et al., "Microglial precursors derived from mouse embryonic stem cells", Glia 57, (2009), pp. 1660-1671.

Nimmerjahn, A., "Two-photon imaging of microglia in the mouse cortex in vivo", Cold Spring Harbor protocols, (2012), pp. 594-603.

Nimmerjahn, A., et al., "Resting microglial cells are highly dynamic surveillants of brain parenchyma in vivo", Science 308, (2005), pp. I 314-1318.

Pallotta, I et al., "BMP protein-mediated crosstalk between inflammatory cells and human pluripotent stem cell-derived cardiomyocytes", Journal of tissue engineering and regenerative medicine, (2015), 13 pages.

Panicker, L.M., et al., "Gaucher iPSC-derived macrophages produce elevated levels of inflammatory mediators and serve as a new platform for therapeutic development", Stem cells 32, (2014), pp. 2338-2349.

Paolicelli, Rc., et al., "Synaptic pruning by microglia is necessary for normal brain development", Science 333, (2011), pp. 1456-1458.

Paull, D., et al. Automated, high-throughput derivation, characterization and differentiation of induced pluripotent stem cells. Nature Methods 12, (2015), pp. 885-892.

Ransohoff, R. M., "How neuroinflarnmation contributes to neurodegeneration", Science 353, (2016), pp. 777-783.

Ransohoff, R. M., et al., Microglial physiology: unique stimuli, specialized responses, Annual reviewof immunology 27, (2009), pp. 119-145.

Robinson, M.D., et al., "edgeR: a Bioconductor package for differential expression analysis of digital gene expression data", Bioinfonnatics 26, (2010), pp. 139-140.

Schulz, C., et al., "A lineage of myeloid cells independent of Myb and hematopoietic stem cells", Science 336, (2012), pp. 86-90.

Smith, A.M., et al., "The human side of microglia", Trends in neurosciences 37, (2014) pp. 125-135.

Sturgeon, C.M., et al. "Wnt signaling controls the specification of definitive and primitive hematopoiesis from human pluripotent stem cells", Nature biotechnology 32, (2014), pp. 554-561.

Tsuchiya, T., et al., "Characterization of microglia induced from mouse embryonic stem cells and their migration into the brain parenchyma", Journal of neuroimmunology 160, (2005), pp. 210-218.

Ueno, M., et al., "Layer V cortical neurons require microglial support for survival during postnatal development", Nature neuroscience 16, (2013), pp. 543-551.

Vanhee, S., et al., "In vitro human embryonic stem cell hematopoiesis mimics MYB-independent yolk sac hematopoiesis", Haematologica 100, (2015), pp. 157-166.

Woodard, C.M., et al., "iPSC-derived dopamine neurons reveal differences between monozygotic twins discordant for Parkinson's disease", Cell reports 9, (2014), pp. 1173-1182.

Zhahg, Y., et al., "Purification and Characterization of Progenitor and Mature Human Astrocytes Reveals Transcriptional and Functional Differences with Mouse", Neuron 89, (2016), pp. 37-53.

* cited by examiner

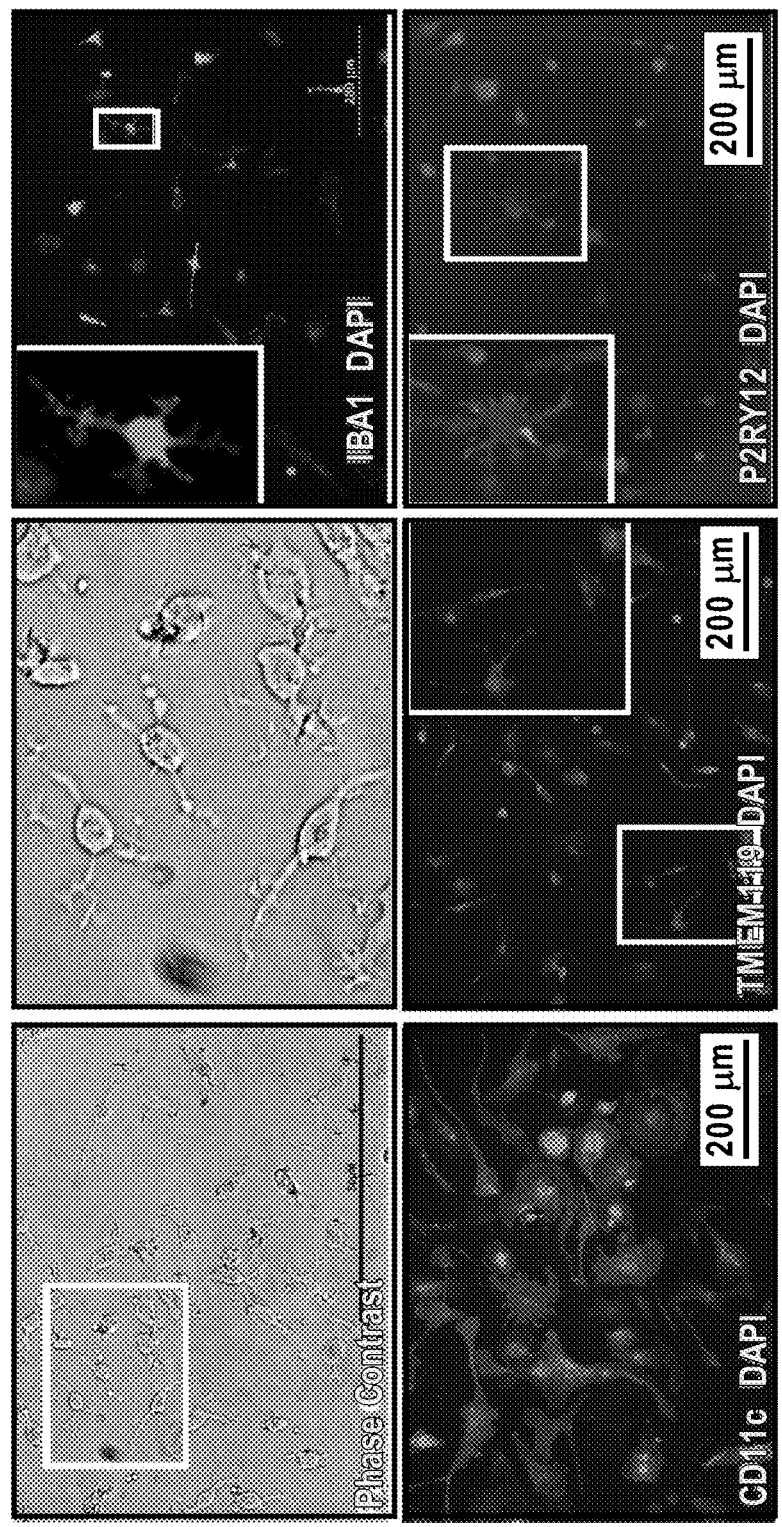

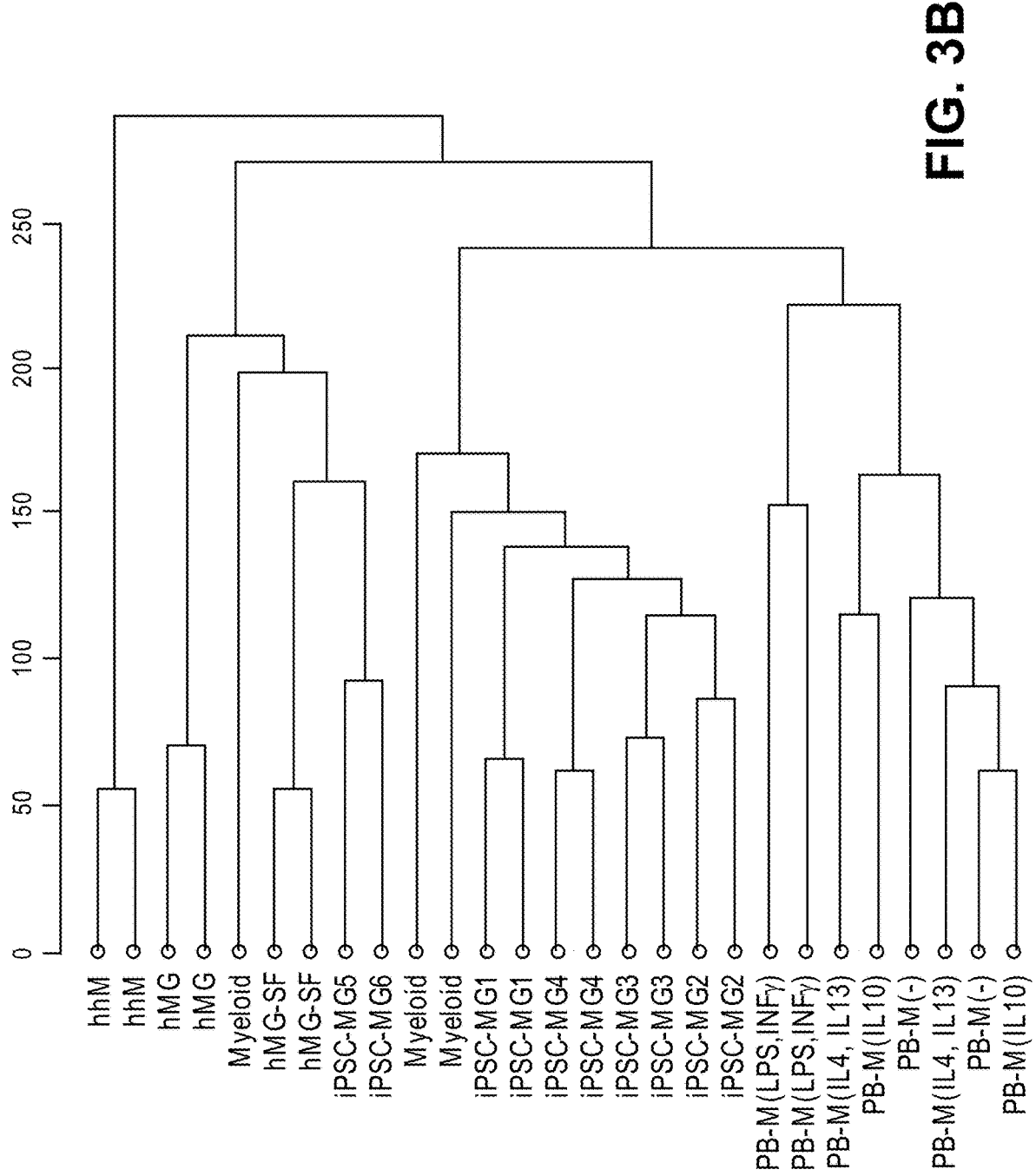

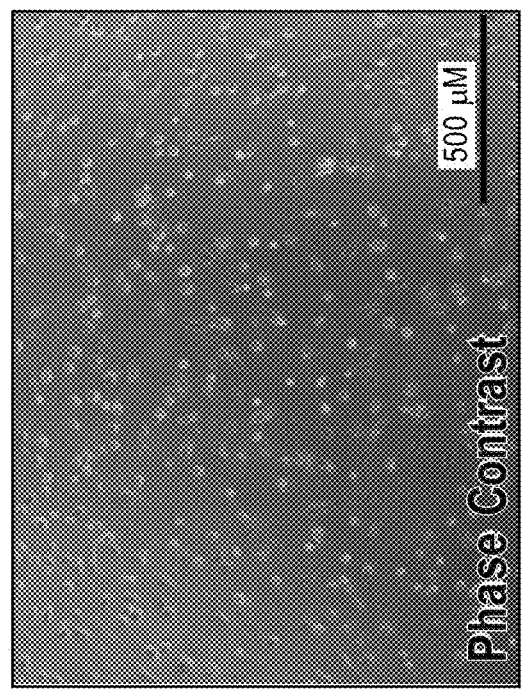
Efficiency of CD14+ myeloid cells
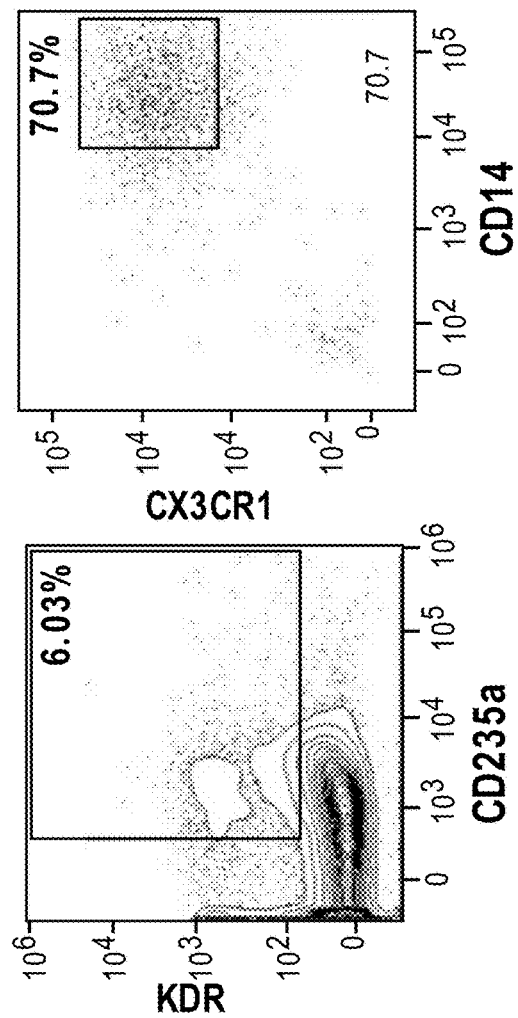
FIG. 5A   FIG. 5B   FIG. 5C

IBA1 CD11C DAPI

MICROGLIA DERIVED FROM PLURIPOTENT STEM CELLS AND METHODS OF MAKING AND USING THE SAME

CROSS-REFERENCE TO RELATED APPLICATIONS

This application claims the benefit of priority of U.S. Provisional Patent Application No. 62/303,301, filed on Mar. 3, 2016 and U.S. Provisional Patent Application No. 62/410,645, filed on Oct. 20, 2016, the contents of each which are hereby incorporated by

STATEMENT REGARDING FEDERALLY SPONSORED RESEARCH

This invention was made with government support under Grant No. R01 AG046170 awarded by the National Institutes of Health. The government has certain rights in the invention.

INCORPORATION BY REFERENCE

For the purpose of only those jurisdictions that permit incorporation by reference, all of the references cited in this disclosure are hereby incorporated by reference in their entireties (numbers in parentheses or in superscript following text in this patent disclosure refer to the numbered references provided in the "Reference List" section of this patent specification). In addition, any manufacturers' instructions or catalogues for any products cited or mentioned herein are incorporated by reference. Documents incorporated by reference into this text, or any teachings therein, can be used in the practice of the present invention.

BACKGROUND OF THE INVENTION

Microglia are the resident, tissue-specific macrophages of the brain. They perform several critical roles in the development and maintenance of the central nervous system (CNS). Microglia arise from primitive CD45+CX3CR1− myeloid progenitors in the yolk sac that differentiate to CD45+CX3CR1+ microglial progenitors and invade the developing brain before the emergence of definitive hematopoiesis. In the healthy, adult brain with an intact blood brain barrier, microglia persist as a long-lived, self-sustained population that is not replenished by circulating bone marrow-derived cells. Highly branched microglia cells, defined as "resting", are in reality highly active as their processes continuously move to examine the brain for homeostatic disruptions.

Microglia use phagocytosis to eliminate pathogens and/or damaged or dead cells, and remove toxic molecules, cellular debris, and/or protein deposits, thus attenuating inflammation and promoting tissue regeneration and repair. During development, microglia promote migration and differentiation of neural progenitors, neurogenesis, and oligodendrogenesis, and regulate synaptogenesis and synaptic plasticity through pruning. Microglia can also contribute to pathological brain inflammation and disruption of the blood-brain barrier by releasing cytokines and neurotoxic molecules. Dysfunctional microglia have been linked to amyotrophic lateral sclerosis (ALS) and Alzheimer's disease (AD). Chronic activation of microglia cells is a possible trigger to the progression of multiple sclerosis (MS) and Parkinson's disease, and defective phagocytosis and synaptic pruning have been implicated in the pathogenesis of schizophrenia and autism spectrum disorders. Other diseases determined to have microglial involvement based on animal studies include Rett syndrome, diffuse leukoenchephalopathy with spheroids (such as hereditary diffuse leukoenchephalopathy with axonal spheroids), and frontotemporal lobar degeneration (FTLD), such as familial FTLD.

Most of our knowledge regarding microglia derives from rodent studies. However, there are major differences between rodent and human microglial cells, such as in their proliferation rates, adhesive properties, and expression of critical receptors. Consistent with these differences, protocols developed previously for the differentiation of rodent pluripotent stem cells into microglia have not been effective with human pluripotent stem cells.

Direct analysis of primary human microglial cells has been severely hampered by the limited availability of human brain specimens, especially from healthy individuals. While the development of the human pluripotent stem cell (PSC) field has enabled the generation of many different differentiated cell types from human pluripotent stem cells, there has remained a need in the art for efficient and reproducible methods for the generation of microglial cells from such human stem cells. The present invention addresses this need.

SUMMARY OF THE INVENTION

Microglia, the immune cells of the brain, are crucial to the proper development and maintenance of the central nervous system, and are involved in numerous neurological diseases and disorders. The present invention provides various new and improved methods for the generation of human microglia from pluripotent stem cells. Using chemically defined media, the methods of the present invention are used to generate microglial progenitors expressing CD14 and/or CX3CR1 from both embryonic stem cells (ES cells or ESCs) and induced pluripotent stem cells (iPS cells or IPSCs). Such microglial progenitors typically appear within around 25-30 days and continue to be produced for around 20-25 days—until around day 50. The methods provided herein also enable the further differentiation of such microglial progenitors—resulting in the generation of ramified microglia that have highly motile processes, express many typical microglial markers, release cytokines, have phagocytotic activity, and respond to ADP by producing intracellular $Ca^{2+}$ transients. These methods are highly reproducible across different pluripotent stem cell (PSC) lines.

Some of the main aspects of the present invention are summarized below. Additional aspects are described in the Detailed Description of the Invention, Examples, Figures, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the invention.

In some embodiments the present invention provides methods for generating microglial cells from pluripotent stem cells. In some such embodiments the pluripotent stem cells are from any mammalian species. In some embodiments the pluripotent stem cells are human pluripotent stem cells—resulting in the generation of human microglial cells. In some embodiments the pluripotent stem cells are either induced pluripotent stem cells ("iPS cells" or "iPSCs"), or embryonic stem cells ("ES cells" or "ESCs"). Such methods involve two main steps. In the first step, the pluripotent stem cells are cultured under conditions that induce myeloid differentiation, leading to the generation of CD14+ and/or CX3CR1+ microglial progenitor cells. In the second step, the CD14+ and/or CX3CR1+ microglial progenitor cells are differentiated into microglial cells. In some embodiments the CD14+ and/or CX3CR1+ microglial progenitor cells are differentiated into microglial cells by culturing them in either (i) a first microglial differentiation medium comprising IL-34, or (ii) a second microglial differentiation medium comprising M-CSF. In some embodiments the first microglial differentiation medium also comprises GM-CSF. In some embodiments the second microglial differentiation medium also comprises one or more factors selected from the group consisting of GM-CSF, NGF-β and CCL2. For example, in some embodiments the second microglial differentiation medium also comprises each of GM-CSF, NGF-β and CCL2. In some embodiments the CD14+ and/or CX3CR1+ microglial progenitor cells are contacted with the first or second microglial differentiation medium for around 15 days. In some embodiments, the CD14+ and/or CX3CR1+ microglial progenitor cells generated in the first step are isolated before proceeding to the second step. In some embodiments the microglial progenitor cells are isolated at around the time that CD14 expression peaks.

In some alternative embodiments, the present invention provides methods for generating microglial progenitor cells from pluripotent stem cells. Such methods involve performing the first of the two main steps described above, including, optionally, isolating the resulting CD14+ and/or CX3CR1+ microglial progenitor cells.

In other alternative embodiments, the present invention provides methods for generating microglial cells from microglial progenitor cells. Such methods involve performing the second of the two main steps described above.

In some of the embodiments of the present invention that involve culturing pluripotent stem cells under conditions that induce myeloid differentiation (leading to the generation of CD14+ and/or CX3CR1+ microglial progenitor cells), a multi-step process is used in which the cells are cultured with different combinations of cytokines and tissue culture media at each stage. Steps in these multi-step processes may result in inducing differentiation of pluripotent stem cells into primitive hemangioblasts, and/or inducing differentiation of primitive hemangioblasts into myeloid progenitors, and/or inducing differentiation of myeloid progenitors into microglial progenitors. As defined by their cell surface marker profiles, in some embodiments such multi-step processes may result in first inducing differentiation of the pluripotent stem cells into KDR+ CD235 a+ cells, then into CD45+CX3CR1− cells, and then into CD45+CX3CR1+ CD14+ cells.

In some embodiments, the methods provided herein for the generation of CD14+ and/or CX3CR1+ microglial progenitor cells from pluripotent stem cells comprise performing one or more of the following four steps: First, contacting a cell culture with a first composition comprising BMP4 in a culture medium, wherein when the cell culture is initially contacted with the first composition the cell culture comprises pluripotent stem cells; Second, contacting the cell culture with a second composition comprising one or more of bFGF, SCF, and VEGFA (for example each of bFGF, SCF, and VEGFA) in a hematopoietic cell medium; Third, contacting the cell culture with a third composition comprising one or more of SCF, IL-3, TPO, M-CSF, and FLT3 ligand (for example each of SCF, IL-3, TPO, M-CSF, and FLT3 ligand) in a hematopoietic cell medium; and Fourth contacting the cell culture with a fourth composition comprising one or more of M-CSF, FLT3 ligand, and GM-CSF (for example each of M-CSF, FLT3 ligand, and GM-CSF) in a hematopoietic cell medium. In some embodiments all of the above four steps are performed in order. In some of such embodiments the medium used for any of these four steps is a serum free medium. In some of such embodiments the medium used for any of these four steps is a chemically-defined medium. Exemplary amounts of the agents used in these four compositions are provided in the Detailed Description and Examples sections of this patent disclosure.

In the first of the above four steps, in some embodiments a tissue culture medium suitable for maintenance of stem cells is used, while in other embodiments a tissue culture medium suitable for differentiation of stem cells is used. In some embodiments a modified pluripotent stem cell maintenance medium that does not comprise pluripotency factors is used. In some embodiments a medium does not comprise pluripotency factors is used. For example, in one embodiment, the medium used in the first of the above four steps does not comprise lithium chloride, GABA, pipecolic acid, bFGF or TGFβ1. For example, in one embodiment a modified "mTeSR1" medium that does not contain lithium chloride, GABA, pipecolic acid, bFGF or TGFβ1 is used. In the last three of the above four steps, any suitable hematopoietic cell medium can be used. In one embodiment the hematopoietic cell medium is "StemPro-34."

The present invention also provides certain exemplary timings for performing each of the four steps described above for the generation of CD14+ and/or CX3CR1+ microglial progenitor cells from pluripotent stem cells. These exemplary timings are described in the Detailed Description, the Examples and in the Figures. For example, in some embodiments the cell cultures are contacted with the first composition for approximately 4 days. In some embodiments the cell cultures are contacted with the second composition for approximately 2 days. In some embodiments the cell cultures are contacted with the third composition for approximately 8 days. In some embodiments the cell cultures are contacted with the fourth composition for approximately 11 to 36 days, or more.

In some embodiments, when carrying out the methods described above or elsewhere herein for the generation of CD14+ and/or CX3CR1+ microglial progenitor cells from pluripotent stem cells, instead of discarding the tissue culture supernatant when performing media changes, the supernatant is saved and the cells present in the supernatant are recovered and added back to the cell cultures. This is advantageous because the inventors have discovered that certain of the key cell types induced during the conversion of pluripotent stem cells to microglial progenitors are found predominantly in the cell supernatants—as opposed to being in the layer of cells that adheres to the cell culture plates. Thus, in some embodiments, when media is changed cells present in the culture supernatant are recovered and added back to the cell cultures. In some embodiments, for media exchanges performed after about day 10, cells present in the culture supernatant are recovered and added back to the cell cultures. In some embodiments, for media exchanges performed when the cells are in contact with the third composition or the fourth composition, cells present in the culture supernatant are recovered and added back to the cell cultures. In some embodiments, for media exchanges performed after the emergence of a CD45+CX3CR1− cell population, cells present in the culture supernatant are recovered and added back to the cell cultures.

In some embodiments the present invention provides microglial cells or microglial progenitor cells, such as those produced by the methods described herein. In some embodiments the present invention provides "substantially pure" populations of such cells.

In some embodiments the present invention provides CD14+ microglial progenitor cells, such as those produced by the methods provided herein. In some embodiments the present invention provides CX3CR1+ microglial progenitor cells, such as those produced by the methods provided herein. In some embodiments the present invention provides CD14+CX3CR1+ microglial progenitor cells, such as those produced by the methods provided herein. In some embodiments the present invention provides CD14+CX3CR1+ CD45+ microglial progenitor cells, such as those produced by the methods provided herein.

In some embodiments the present invention provides microglial cells, such as those produced by the methods provided herein, that express one or more markers selected from the group consisting of CD11b, CD11c, CX3CR1, P2RY12, IBA-1, TMEM119, and CD45.

In some embodiments the present invention provides CD11b+, CD11c+, CX3CR1+P2RY12+CD45+ microglial cells, such as those produced by the methods provided herein.

In some embodiments the present invention provides CD11b+, CD11c+, CX3CR1+P2RY12+CD45+, IBA-1+, TMEM119+ microglial, such as those produced by the methods provided herein.

In some embodiments the present invention provides microglial cells, such as those produced by the methods provided herein, that express lower levels of CD11b, OLFML3 and/or TMEM119 than primary microglial cells.

In some embodiments the microglial cells provided herein have a ramified morphology, and/or have phagocytic activity, and/or produce intracellular Ca2+ transients in response to adenosine diphosphate (ADP) exposure, and/or release cytokines, and/or have a transcriptional profile similar to that of primary microglial cells.

The microglial cells and microglial progenitor cells generated using the methods of the present invention can be used for any desired purpose, including, but not limited to, in research, in drug screening, in animal models (such as models of human disease), in methods of treatment, in studying the effects of their released cytokines (for example on other cell types, such as neurons), in direct or indirect co-cultures with other cell types (e.g. neurons, astrocytes, oligodendrocytes, and/or brain endothelial cells), in producing conditioned media for culture of other cell types (e.g. neurons, astrocytes, oligodendrocytes, and/or brain endothelial cells), in the generation in organ cultures and/or 3 dimensional tissue cultures (such as mini-brains or brain organoids), and the like. One of skill in the art will recognize that the microglial cells and microglial progenitor cells described herein, and/or those produced using the methods described herein, can be used for any purpose for which it is, or would be, desirable to use any other microglial cell or microglial progenitor cell.

For example, in some embodiments the present invention provides methods of treatment and methods of prevention comprising administering a microglial cell or microglial progenitor cell as described herein, or as produced using a method described herein, to a subject in need thereof. In some embodiments the subject may have, or be suspected of having, or be at risk of developing, a disease or disorder associated with a defect in or deficiency of microglial cells or microglial progenitor cells. Such diseases and disorders include, but are not limited to amyotrophic lateral sclerosis (ALS), Alzheimer's disease (AD), multiple sclerosis (MS), Parkinson's disease, Rett syndrome, diffuse leukoenchephalopathy with spheroids (such as Hereditary Diffuse Leukoenchephalopathy with Axonal Spheroids), frontotemporal lobar degeneration (FTLD), such as familial FTLD, schizophrenia and autism spectrum disorders. In some such methods the microglial cell or microglial progenitor cell used in treatment is generated from an induced pluripotent stem cell derived from the same subject—i.e. it is an autologous cell. In other such embodiments the microglial cell or microglial progenitor cell used in treatment is generated from a different individual (a donor) of the same species, i.e. it is an allogeneic cell. In some embodiments where an allogeneic/donor cell is used, the cell may be derived from a donor individual having a MHC/HLA type that matches that of the subject.

In other embodiments the present invention provides methods of drug screening using microglial cells or microglial progenitor cells as described herein, or as produced using the methods described herein, including, but not limited to, high-throughput screening methods. For example, in one embodiment the present invention provides a method of identifying a compound useful in the treatment or prevention of a disease or disorder associated with a defect in or deficiency of microglial cells or microglial precursor cells, the method comprising: contacting a microglial cell or microglial progenitor cell as described herein, or as generated using a method described herein, with one or more candidate compounds, and determining whether any one or more of the candidate compounds improves the defect in or deficiency of microglial cells or microglial precursor cells. In some embodiments the present invention provides screening methods aimed at identifying modulators of the P2RY12 G-protein-coupled receptor expressed by the microglial cells described herein, or expressed by the microglial cells generated using the methods described herein. Such methods may comprise contacting such microglial cells with one or more candidate compounds, and determining whether any of the candidate compounds modulate the activity of the P2RY12 G-protein-coupled receptor.

In other embodiments the present invention also provides tissue culture media, tissue culture media supplements, and various kits useful in performing the various methods described herein—as described further in the Detailed Description section of this patent disclosure.

BRIEF DESCRIPTION OF THE FIGURES

The skilled artisan will understand that the drawings are for illustration purposes only, and are not intended to limit the scope of the present teachings.

DETAILED DESCRIPTION OF THE INVENTION

Figure 1A:
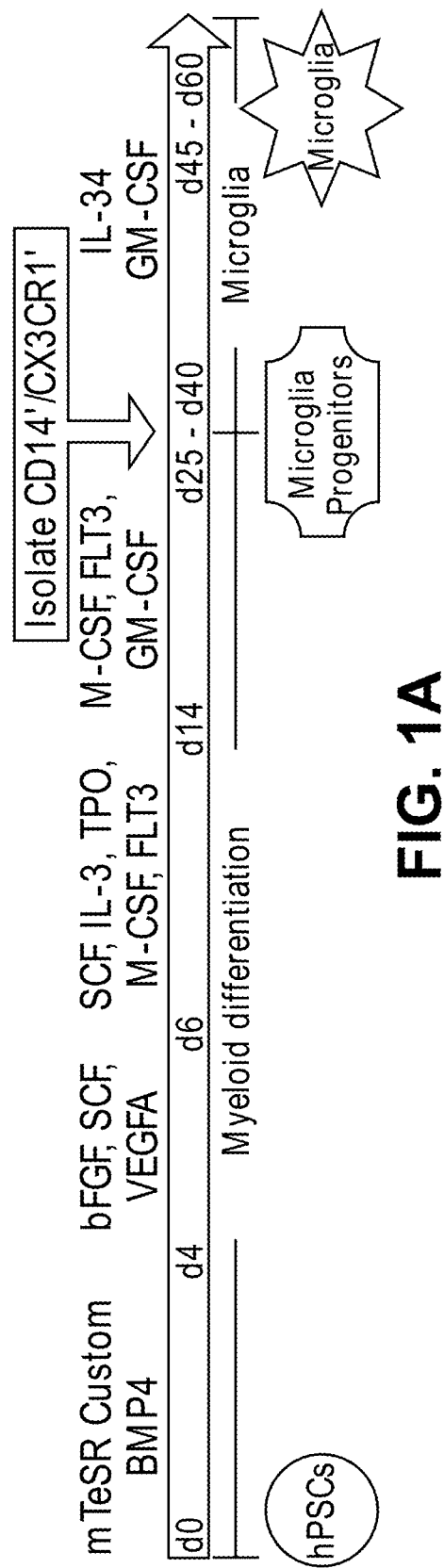
FIG. 1 A-B. PSCs differentiate to microglia through myeloid progenitors. (A) Schematic illustration of the major steps of the microglial differentiation protocol of the present invention. (B) Kinetics of CD45, CX3CR1 and CD14 expression between day 10 and day 25 in the adherent and supernatant fractions.

Some of the main aspects of the present invention are summarized above in the Summary of the Invention section of this patent disclosure. Additional aspects are described in the Examples, Figures, and Claims sections of this disclosure. This Detailed Description of the Invention provides certain additional description and is intended to be read in conjunction with, and combined with the disclosure of, all other sections of this patent disclosure. Furthermore, the various embodiments described in each section of this disclosure can be combined in various different ways, and all such combinations are intended to fall within the scope of the invention. Headings and subheadings used anywhere in this patent disclosure are provided for convenience and ease of reference/reading only, and do not denote limitations of the various aspects or embodiments of the invention described herein, which is to be understood by reference to the specification as a whole.

Definitions & Abbreviations

While certain terms are defined immediately below, each of these terms may be more fully defined by their context of use and by reference to the specification as a whole. Terms not specifically defined immediately below may be defined elsewhere in this patent disclosure, of their meanings may be clear from the context in which the terms are used, or else the terms are used in accordance with their usual meaning—as commonly understood by one of ordinary skill in the art to which this invention pertains. For example, The Dictionary of Cell and Molecular Biology (5th ed. J. M. Lackie ed., 2013), the Oxford Dictionary of Biochemistry and Molecular Biology (2d ed. R. Cammack et al. eds., 2008), and The Concise Dictionary of Biomedicine and Molecular Biology, P-S. Juo, (2d ed. 2002) can provide one of skill with general definitions of some terms used herein.

As used in this specification and the appended claims, the singular forms "a," "an," and "the" include plural referents, unless the context clearly dictates otherwise. The terms "a" (or "an"), as well as the terms "one or more," and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Units, prefixes, and symbols are denoted in their Système International de Unites (SI) accepted form. Numeric ranges are inclusive of the numbers defining the range. Wherever embodiments are described with the language "comprising," otherwise analogous embodiments described in terms of "consisting of" and/or "consisting essentially of" are included.

Where a numeric term is preceded by "about" or "around" or "approximately," the term includes the stated number and values ±10% of the stated number.

The term "pluripotent stem cells" or "PSCs" has its usual meaning in the art, i.e., self-replicating cells that have the ability to develop into endoderm, ectoderm, and mesoderm cells. In some embodiments PSCs are human PSCs. PSCs include embryonic stem cells (ESCs) and induced pluripotent stem cells ("iPS cells" or "iPSCs"). The terms ES cells and iPS cells have their usual meaning in the art.

As used herein the phrase "substantially pure" refers to a population of cells wherein at least 95% of the cells have the recited phenotype. In all embodiments that refer to a "substantially pure" cell population, alternative embodiments in which the cell populations have a lower or higher level of purity are also contemplated. For example, in some embodiments, instead of a given cell population being "substantially pure" the cell population may be one in which at least 35%, 40%, 45%, 50%, 55%, 60%, 65%, 70%, 75%, 80%, 85%, 90%, 95%, 96%, 97%, 98%, or 99% of the cells, or 100% of the cells, have the recited phenotype.

By "subject" or "individual" or "patient" is meant any subject, particularly a mammalian subject, for whom diagnosis, prognosis, or therapy is desired, or from whom a microglial cell is to be generated using a method as described herein. Mammalian subjects include humans, domestic animals, farm animals, sports animals, and zoo animals including, e.g., humans, non-human primates, dogs, cats, guinea pigs, rabbits, rats, mice, horses, cattle, pigs, and so on. In some embodiments the subjects are human.

Terms such as "treating" or "treatment" or "to treat" refer to therapeutic measures that cure, slow down, lessen symptoms of, and/or halt progression of a diagnosed pathologic disease or disorder. Thus, those in need of treatment include those already with the disorder. In certain embodiments, a subject is successfully "treated" for a disease or disorder if the subject shows, e.g., total, partial, permanent, or transient, alleviation or elimination of any symptom associated with the disease or disorder.

"Prevent" or "prevention" refers to prophylactic or preventative measures that prevent and/or slow the development of a pathologic disease or disorder. Thus, those in need of prevention include those prone to or susceptible to the disease or disorder. In certain embodiments, a disease or disorder is successfully prevented according to the methods provided herein if the subject develops, transiently or permanently, fewer or less severe symptoms associated with the disease or disorder, or a later onset of symptoms associated with the disease or disorder, than a subject who has not been subject to the methods of the invention.

Additional Description

Various methods for the generation of microglial cells and microglial progenitor cells are described in the Summary of the Invention, Examples, and Claims sections of this patent disclosure. The pluripotent stem cells used in such methods can be any suitable type of pluripotent stem cells. In one embodiment the pluripotent stem cells are ESCs or iPSCs—each of which is well known in the art. Where iPSCs are used, such cells may have been "reprogrammed" to the pluripotent state from a non-pluripotent state using any suitable means known in the art, including, but not limited to, modified RNA-based methods, Sendai virus based methods, and the like. Furthermore, such cells may have been reprogrammed to the pluripotent state using any suitable cocktail of reprogramming factors known in the art.

Unless a specific type of cell/tissue culture media is specified, any suitable cell/tissue culture media known in the art can be used. Many such types of media are known and commercially available. In some embodiments, certain chemically-defined and/or serum free media types are used.

In some embodiments, media suitable for use in maintaining pluripotent stem cells is used. In some such embodiments such a medium is mTeSR1 medium from Stem Cell Technologies. However, one of skill in the art will recognize that there are several other types of media that are equivalent to mTeSR medium in terms of their suitability for use in maintaining pluripotent stem cells—any of which could be used. Typically such media will contain one or more pluripotency factors to facilitate the maintenance of cells in a pluripotent state. In certain embodiments variants of such media are used that do not comprise these pluripotency factors. For example, in certain embodiments where mTeSR1 medium is used, a variant of the mTeSR1 medium (sometimes referred to herein as "mTeSR1 Custom" medium) that does not comprise lithium chloride, GABA, pipecolic acid, bFGF or TGFβ1 is used. The composition of mTeSR1 medium is known in the art and described in, for example, Ludwig et al., 2006 (Nat Methods. 2006 August; 3(8):637-46; "Feeder-Independent Culture of Human Embryonic Stem Cells"), the contents of which are hereby incorporated by reference.

In some embodiments, media suitable for use in differentiating pluripotent stem cells is used. Such media typical do not comprise pluripotency factors.

In some embodiments, media suitable for culturing hematopoietic cells is used. In some such embodiments such the medium is StemPro-34 from ThermoFisher. The composition of StemPro-34 medium is known in the art and described in, for example, EP 0891419 A4 entitled "Hematopoietic Cell Culture Nutrient Supplement" and WO1997033978A1, the contents of which are hereby incorporated by reference. However, one of skill in the art will recognize that there are several other types of media that are equivalent to StemPro-34 medium in terms of their suitability for use in culturing hematopoietic cells—any of which could be used.

Many of the embodiments of the present invention involve certain factors to be used in (or excluded from) the compositions and methods described herein, for example as media supplements. These include, but are not limited to, bFGF, SCF, VEGFA, IL-3, TPO, M-CSF, FLT3 ligand, GM-CSF, GABA, pipecolic acid, bFGF, TGFβ1, IL-34, GM-CSF, M-CSF, NGF-β and CCL2. Each of these factors is well known in the art, including the full names of each of these factors in the cases where acronyms or other abbreviations are used. Furthermore, all of these factors are available to the public from multiple sources, including commercial sources. Exemplary amounts/concentrations for use of each of these factors in the methods and compositions of the present invention are provided in the Examples section of this patent disclosure. For all embodiments where specified amounts are referred to, amounts that are "about" the specified amount are also intended. Furthermore, one of skill in the art will recognize that in some situations further deviations from the specified amounts can be used, and will be able to determine how much of each factor to use by performing routine testing, optimization, dose-response studies, and the like, for example to reduce or increase the specified amounts, as long as the amounts used still achieve the stated effect—e.g. the stated differentiation effect. For example, in some embodiments specified amounts of the specified agents may be reduced to 10%, or 20%, or 30%, or 40%, or 50%, or 60%, or 70%, or 80%, or 90% of the stated amounts. Similarly, in some embodiments the specified amounts of the specified agents may be increased by 10%, by 20%, by 30%, by 40%, by 50%, by 60%, by 70%, by 80%, by 90%, by 100%, by 150%, by 200%, by 300%, by 400%, or by 500% of the stated amounts. Similarly, where specified factors are referred to, one of skill in the art will recognize that analogs, variants, or derivatives of such factors can also be used as long as the analogs, variants, or derivatives have the same general function/activity as the specified factors.

Similarly, where exemplary times/timing for using of each of these factors, or indeed for performing any other step of any method provided herein, are specified, times/timing that is "about" the specified time is also intended. Furthermore, one of skill in the art will recognize that in some situations further deviations from the specified times/timing can be used, and will be able to determine how the time can be adjusted by performing routine testing, optimization, dose-response studies, and the like, for example to reduce or increase the specified times/timing as long as the times/timing still achieves the stated effect—e.g. the stated differentiation effect. For example, in some embodiments specified times may be reduced to 10%, or 20%, or 30%, or 40%, or 50%, or 60%, or 70%, or 80%, or 90% of the stated times. Similarly, in some embodiments the specified times may be increased by 10%, by 20%, by 30%, by 40%, by 50%, by 60%, by 70%, by 80%, by 90%, by 100%, by 150%, by 200%, by 300%, by 400%, or by 500% of the stated times.

Unless otherwise stated herein, routine and well known methods and compositions for cell culture are to be used in carrying out the methods of the present invention, including routine methods for preparing media, exchanging media, spinning down supernatants to recover non-adherent cells, etc. In some embodiments the culture methods of the present invention used for the generation of microglia or microglial progenitors from pluripotent stem cells employ monolayer cultures. In other embodiments the culture methods of the present invention used for the generation of microglia or microglial progenitors from pluripotent stem cells do not employ the use of feeder cells/feeder layers. In further embodiments the culture methods of the present invention used for the generation of microglia or microglial progenitors from pluripotent stem cells do not employ, and/or do not require, embryoid body (EB) formation.

Many of the embodiments of the present invention describe cell populations in terms of their expression of certain cell markers. These markers include, but are not limited to, CD14, CX3CR1, CD11b, CD11c, P2RY12, IBA-1, and TMEM119. Each of these markers is well known in the art, including the full names of each of these markers—in the cases where acronyms or other abbreviations are used. When any of these markers is referred to with a "+" symbol (e.g. marker+, e.g. CD14+), the "+" symbol means that the cell is positive for that marker—i.e. expresses detectable levels of that marker. One can determine if a cell expresses a detectable level of any of these markers using standard and routine methods known in the art, including those involving antibody-based detection, mRNA detection, and the like.

Several of the methods described herein involve isolating/separating CD14+ and/or CX3CR1+ microglial progenitor cells from other cell types. In some embodiments these methods involve contacting the cells (e.g. a mixed cell population) with an anti-CD14 antibody and/or a CX3CR1 antibody. Then any suitable method known in the art can be used to separate cells bound by the antibody from cells not bound by the antibody. One such method is fluorescence activated cell sorting (FACS). Other suitable methods include those that utilize magnetic beads. Such methods typically involve contacting with both the desired antibody and with magnetic beads, wherein the magnetic beads are constructed such that they can directly or indirectly bind to the antibody. Then, a magnet can be used to separate cells bound by the antibody from cells not bound by the antibody. Any suitable anti-CD14 antibody or anti-CX3CR1 antibody know in the art can be used. Exemplary antibodies are listed in the Examples section of this patent application. Furthermore, an exemplary commercially available kit for magnetic bead based isolation of CD14+ cells is identified in the Examples section of this patent application.

In some embodiments the present invention provides tissue culture media, tissue culture media supplements, and various kits useful in performing the various methods described herein.

In one embodiment, the present invention comprise a kit for generating microglial progenitor cells from pluripotent stem cells, the kit comprising any two or more factors selected from the group consisting of: BMP4, bFGF, SCF, VEGFA, SCF, IL-3, TPO, M-CSF, FLT3 ligand, M-CSF, and GM-CSF. In some embodiments the kit comprises each of these factors.

In one embodiment, the present invention comprise a kit for generating microglial progenitor cells from pluripotent stem cells, the kit comprising any two or more factors selected from the group consisting of: BMP4, bFGF, SCF, VEGFA, SCF, IL-3, TPO, M-CSF, FLT3 ligand, M-CSF, and GM-CSF, IL-34, NGF-β and CCL2. In some embodiments the kit comprises each of these factors.

In some embodiments such kits comprise one or more media supplement compositions, each present in a separate container, selected from the group consisting of: (a) a first media supplement/composition comprising BMP4, (b) a second media supplement/composition comprising: one or more of (e.g. each of) bFGF, SCF, and VEGFA, a third media supplement/composition comprising: one or more of (e.g. each of) SCF, IL-3, TPO, M-CSF, and FLT3 ligand, a fourth media supplement/composition comprising: one or more of (e.g. each of) M-CSF, FLT3 ligand, and GM-CSF, and a fifth media supplement/composition comprising: either (i) one or more of (e.g. each of) GM-CSF and IL-34 or (ii) one or more of (e.g. each of) M-CSF, GM-CSF, NGF-β and CCL2. Where the kit is to be used for preparation of microglial progenitors, each of the first to fourth media supplements/compositions may be included in the kit. Where the kit is to be used for preparation of microglial cells, all five media supplements/compositions may be included in the kit.

The kits described herein may also comprise tissue culture medium, such as a medium suitable for the maintenance or differentiation of pluripotent stem cells, and/or a hematopoietic cell medium. In some embodiments the medium does not comprise pluripotency factors.

The kits described herein may also include an anti-CD14 antibody, an anti-CX3CR1 antibody, or both an anti-CD14 antibody and an anti-CX3CR1 antibody.

The kits may optionally comprise instructions for use, one or more containers, one or more antibodies, or any combination thereof. A label typically accompanies the kit, and includes any writing or recorded material, which may be electronic or computer readable form (e.g., disk, optical disc, memory chip, or tape) providing instructions or other information for use of the kit contents.

In some embodiments the present invention also provides tissue culture media, which may optionally be provided with certain media supplements. For example, in one embodiment the present invention provides a medium suitable for use in maintaining pluripotent stem cells, wherein the medium does not comprise pluripotency factors. For example, in some such embodiments the medium does not comprise lithium chloride, GABA, pipecolic acid, bFGF or TGFβ1. Optionally, such media may comprise, or be provided with, BMP4 as a media supplement. In another embodiment the present invention provides a medium suitable for culture of hematopoietic cells. Optionally, such media may comprise, or be provided with, a media supplement/composition comprising: one or more of (or each of) bFGF, SCF, and VEGFA; and/or a media supplement/composition comprising: one or more of (or each of) SCF, IL-3, TPO, M-CSF, and FLT3 ligand; and/or a media supplement/composition comprising: one or more of (or each of) M-CSF, FLT3 ligand, and GM-CSF. In some such embodiments the media is serum free media. In some such embodiments the media is a chemically-defined media.

The practice of the present invention will employ, unless otherwise indicated conventional techniques of cell biology, molecular biology, cell culture, immunology and the like which are in the skill of one in the art. These techniques are fully disclosed in the current literature and reference is made specifically to Sambrook, Fritsch and Maniatis eds., "Molecular Cloning A Laboratory Manual, 2nd Ed., Cold Springs Harbor Laboratory Press, 1989); the series Methods of Enzymology (Academic Press, Inc.); and Antibodies: A Laboratory Manual, Harlow et al., eds., (1987).

EXAMPLES

Example 1—Generation of Microglia from Human Pluripotent Stem Cells

Figure 5D:
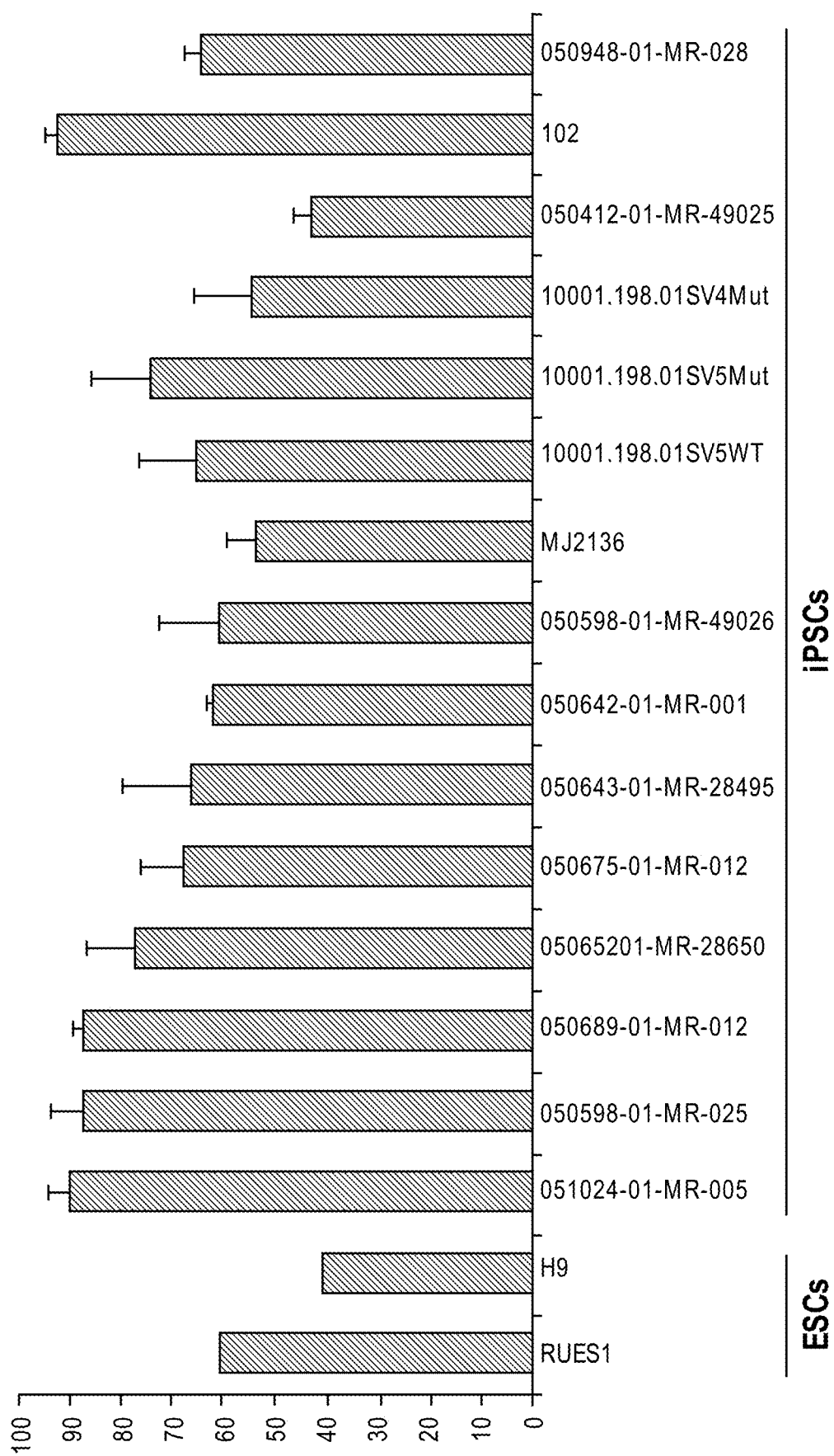
FIG. 5 A-D. Microglial progenitors. (A) Primitive hemagioblasts could be identified as KDR+CD235a+ in the adherent fraction of day 6 cultures. (B) Representative plot of the sorting gate used to isolate CD14+CX3CR1+ microglial progenitors via FACS between day 25 and 50 of differentiation. (C) Phase contrast image of plated microglial progenitors two days after isolation. Scale bar is 500 µm. (D) Graph showing the performance of 2 ESC and 15 iPSC lines in generating CD14+ myeloid progenitors, quantified by flow cytometry.

As microglia cells arise from myeloid progenitors in the yolk sack during embryonic development, we sought to establish a serum- and feeder-free protocol to differentiate human PSCs towards the myeloid lineage. The protocol that we generated is illustrated in schematic form in FIG. 1A). Building upon previous studies (Yanagimachi et al., 2013), we induced primitive streak-like cells through BMP4 signaling, obtaining a KDR+CD235a+ population of primitive hemangioblasts (Sturgeon et al., 2014) (FIG. S1A). CD45+ CX3CR1− microglial progenitors appeared in the supernatant fraction of the culture by day 16, while CX3CR1 was upregulated between day 20 and 25. In contrast, the adherent population contained only a small fraction of CD45+ CX3CR1+ progenitors. Interestingly, a subset of the CD45+ CX3CR1− population upregulated CD14 around day 16, before the upregulation of CX3CR1 (FIG. 1B). Between day 25 and day 50, 82±5% of the CD14+ cells co-expressed CX3CR1. The protocol's efficiency to generate microglial progenitors, based on CD14 expression, was 68±4% across seventeen lines tested (FIG. 5D), which included two ESC and fifteen iPSC lines. Microglial progenitors were continuously generated in the supernatant fraction for up to one month and they were isolated once per week with an average yield of 224±42×10³ cells per isolation, for every 100×10³ PSCs plated. Microglial progenitors were isolated either via FACS sorting (FIG. 5 B, C) or magnetic bead-based separation for further differentiation or for long-term storage in liquid nitrogen. Thawed progenitors retained their differentiation capacity, with a post-thaw viability of 57±5%.

Generation of Microglia

Figure 1B:
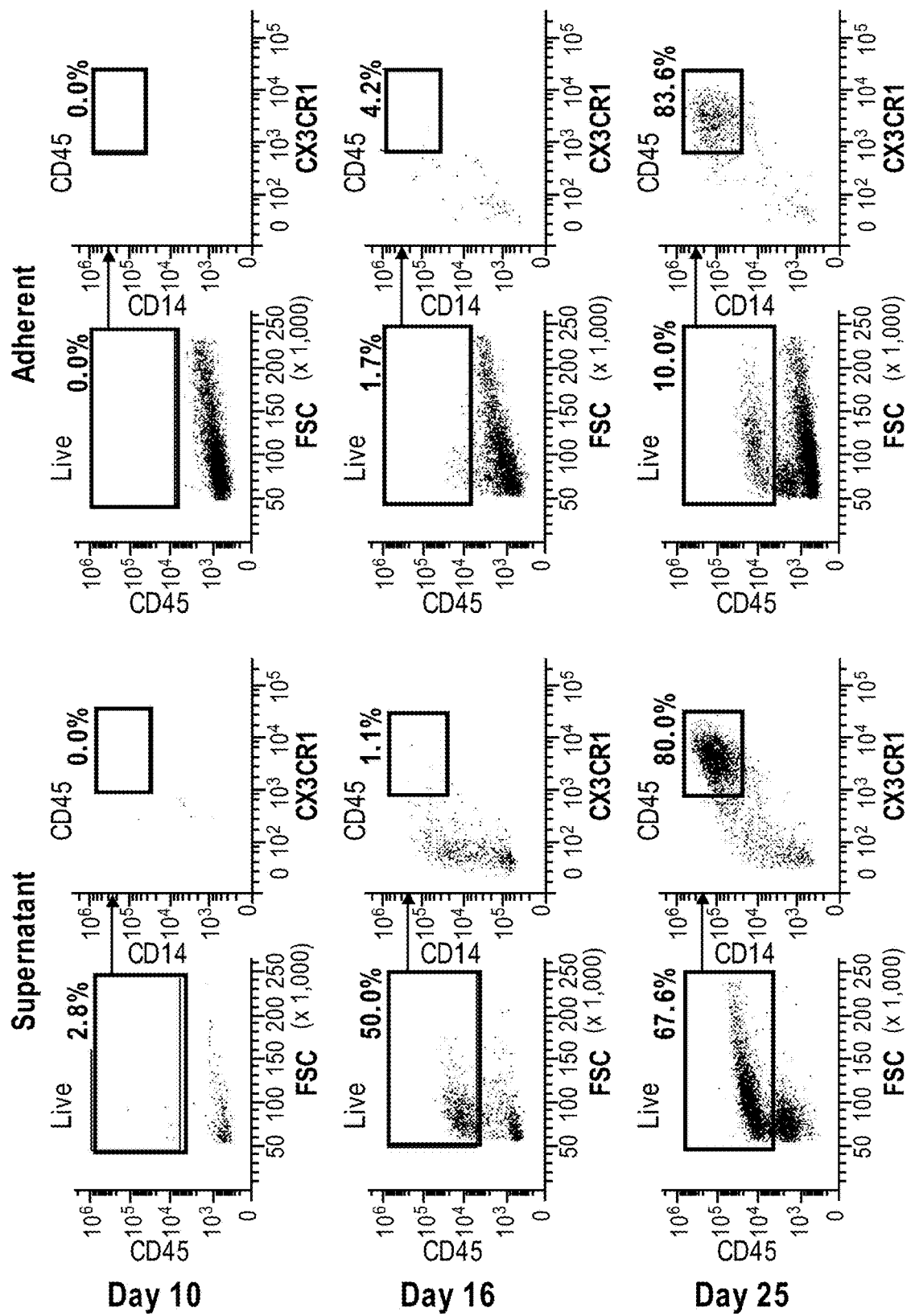
Figure 2B:
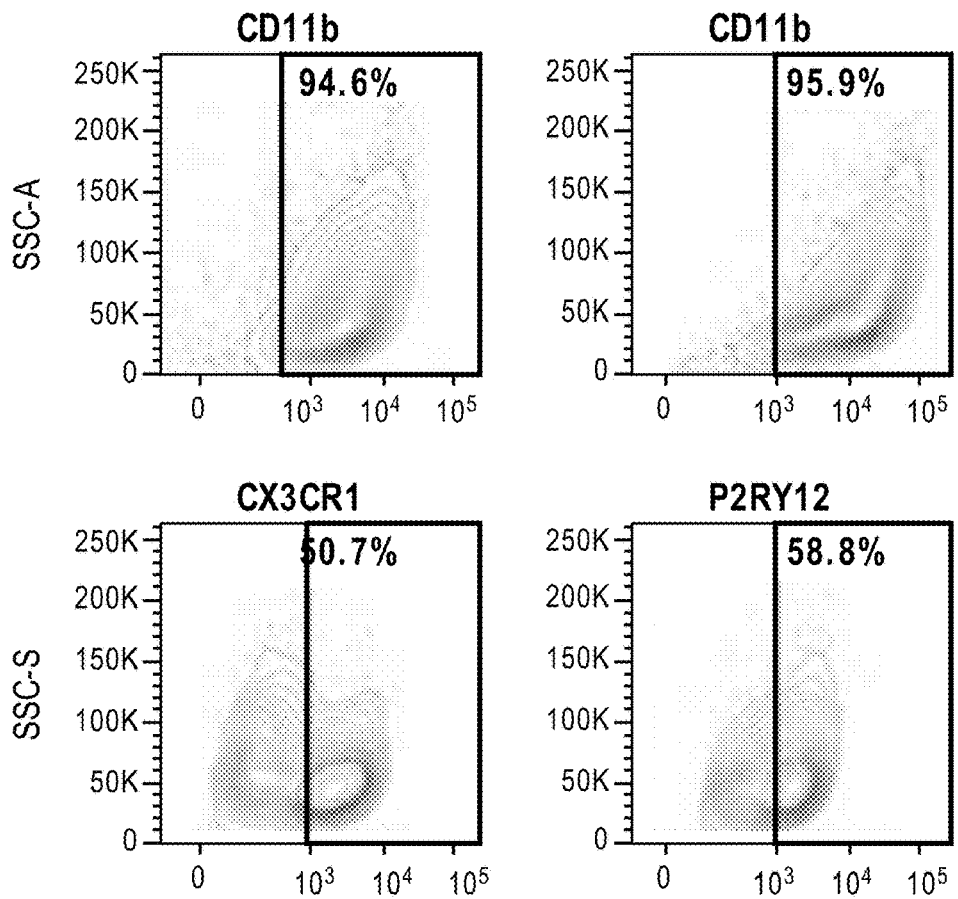
FIG. 2 A-C. Characterization of iPSC-MG. (A) Panel of representative images of iPSC-MG in phase contrast and after immunofluorescent labeling for IBA1, CD11c, TMEM119 and P2RY12. White boxes indicate the areas of the magnified insets. Scale bars are 50 μm, 200 μm, 200 μm, 200 μm and 200 μm. (B) Flow cytometry plots for typical microglial surface antigens in iPSC-MG. (C) Dot-plot showing the percentage of total cells expressing the microglial surface antigens shown in B across 4 independent iPSC-MG (depicted as circles) and 2 hMG samples (depicted as triangles). Error bars indicate the mean±SEM.
Figure 2C:
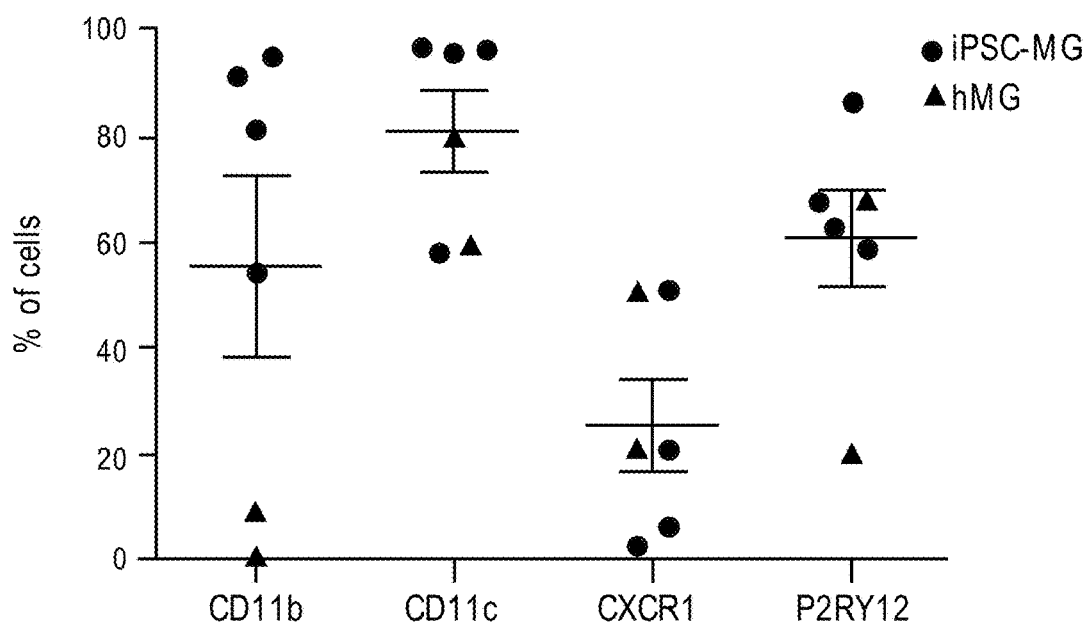
Figure 6:
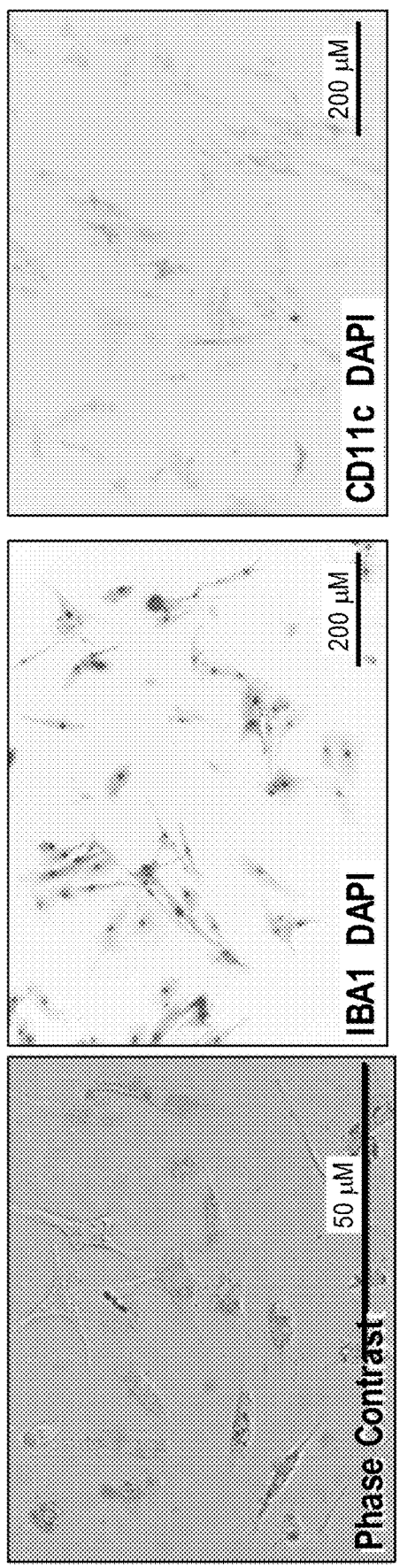
FIG. 6. Characterization of human primary microglia (hMG). Panel of representative images of hMG in phase contrast, and after immunofluorescent labeling for IBA1 and CD11c. Scale bars from left to right are 500 µm, 200 µm and 200 µm.

The protocol that we developed for generation of microglia is illustrated in schematic form in FIG. 1A). Microglial progenitors were produced from iPSCs as described in Example 1. IL-34 and GM-CSF stimulation for two weeks induced the differentiation of isolated microglial progenitors into microglia. The iPSC-derived microglia cells (iPSC-MG) grew as adherent cells, extended many processes and exhibited morphology typical of microglial cells (FIG. 2A). Furthermore, time-lapse video microscopy of iPSC-MG showed their processes to be highly motile, constantly scanning the microenvironment, similarly to microglia cells in vivo (Davalos et al., 2005; Nimmerjahn, 2012). iPSC-MG expressed known antigenic markers including IBA-1, CD11c, TMEM119, P2RY12, CD1 lb and CX3CR1 (FIG. 2A-C). Of note, Thermanox plastic coverslips seemed to provide the optimal surface environment as cells appeared more ramified. Commercially available human primary microglia cells (hMG) were used for comparison (FIG. 6).

iPSC-Derived Microglia Resemble Human Primary Microglia

Figure 3A:
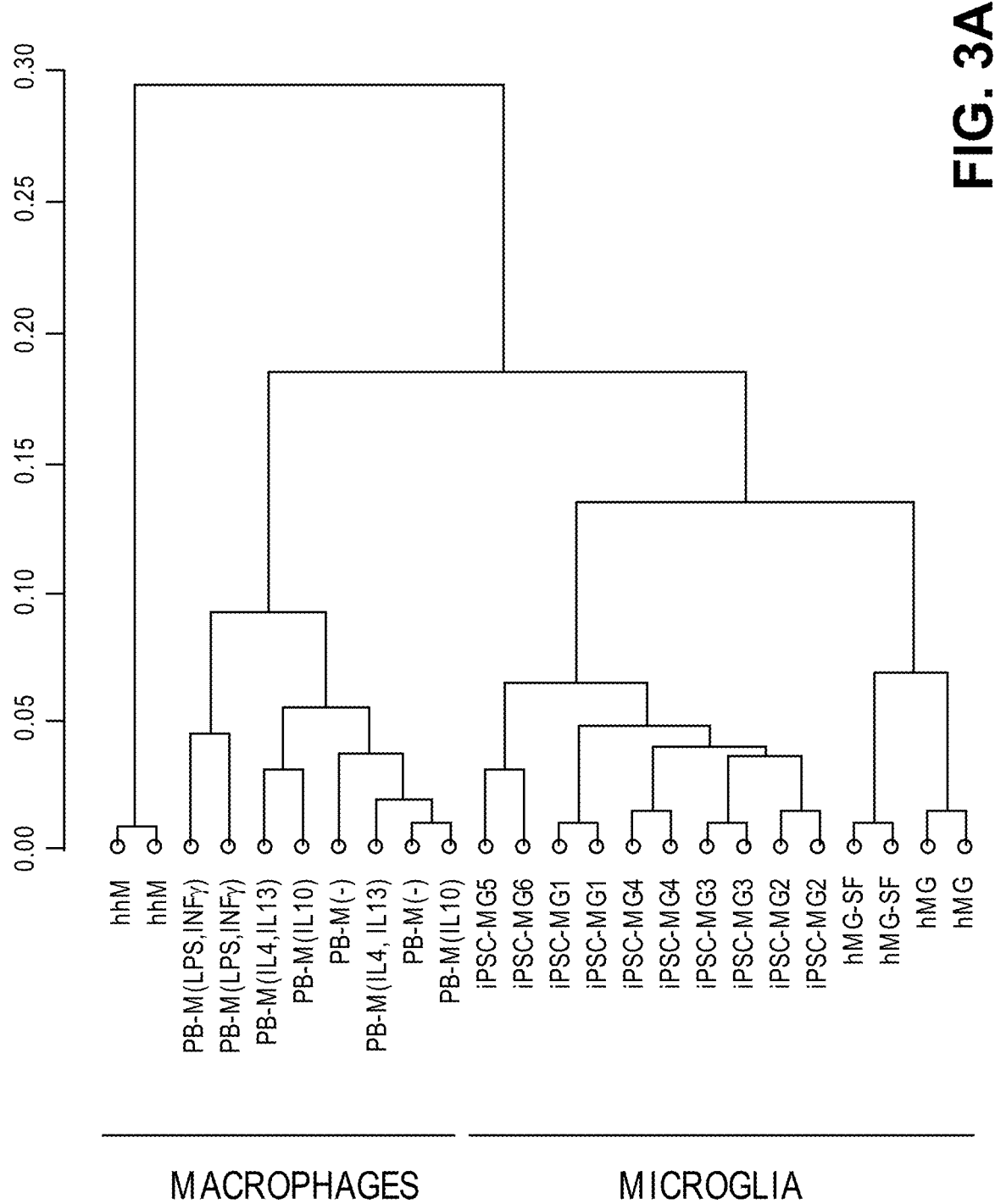
FIG. 3 A-E. Gene expression, cytokine release profile, and phagocytosis of microglia and macrophages. (A) Hierarchical clustering dendrogram of the RNAseq data based on global mRNA expression. Sample distances were calculated from Pearson's correlation coefficient analysis. (B) Dendrogram showing hierarchical clustering of our RNAseq data and data obtained from an independent study of human primary CD45+ cells in the brain ("Myeloid", GEO: GSE73721). Analysis is based on transcriptome-wide expression. (C) Graphs showing the expression levels of the six human microglial signature genes. Samples correspond to data from independent studies (GSE73721, GSE85839). (D) Heat-map of the released cytokine profiles of 5 independent iPSC-MG runs from 2 lines, 2 independent hMG samples and one hMG-SF sample compared to PB-M. Arrows indicate the 5 proteins upregulated in hMG and M(LPS, IFNγ) only. (E) Representative fluorescent image and flow cytometry histograms showing phagocytosis of YG-labeled microspheres. iPSC: Undifferentiated iPSCs used as negative control.

To further confirm the identity of iPSC-MG, whole transcriptome analysis was performed with next generation deep RNA sequencing (RNAseq). iPSC-MG from six unrelated healthy donors were compared to peripheral blood-derived macrophages (PB-M(−)), macrophages polarized to M(LPS, IFNγ), M(IL4, IL13) and M(IL10), primary human hepatic macrophages (hhM) and primary human microglia cultured in serum-containing media supplied by the provider (hMG) or in our serum-free media (hMG-SF). We obtained high quality sequencing reads (mean Phred quality score >38.4) of which more than 86.2% mapped to human genome hg19 by the STAR aligner. A total of 18,516 genes were considered expressed and used for further analysis.

iPSC-MG, hMG and hMG-SF clustered together in a hierarchical cluster analysis using all the expressed genes showing high degree of similarity at the global gene expression level (Spearman's correlation coefficient 0.901~0.997) and were distinct from all macrophage subtypes (FIG. 3A). We then performed hierarchical cluster analysis including data obtained from an independent study (Zhang et al., 2016) that isolated primary CD45+ cells from human brain extracts (termed "Myeloid" in FIG. 3B). The iPSC-MG samples clustered together with the "Myeloid" samples, while PB-M created a distinct cluster and hhM clustered separately, appearing the most dissimilar to any of the tested samples.

Three recent studies (Bennett et al., 2016; Butovsky et al., 2014; Hickman et al., 2013) have provided datasets with unique genes expressed in microglia from primary rodent cells. We next selected genes that were identified in at least two of these studies and assessed their expression in our samples (Table 1).

Of the 31 selected genes, 29 were expressed (defined as at least 1 CPM) by hMG and 28 by iPSC-MG. Overall, the expression levels of these genes were comparable with the exception of P2RY13, which was 2.6 times less in iPSC-MG and CYSLTR1, which was 3.8 times less in hMG. Moreover, LIPH had very low expression (<1 CPM) in all human cell types tested, while hMG showed low expression of CX3CR1, and iPSC-MG low expression of TMEM119 and LAG3. However, CX3CR1 and TMEM119 proteins were detected by FACS and immunofluorescent staining respectively.

Comparisons with tissue-resident hepatic macrophages and peripheral blood-derived macrophages highlighted 11 genes (TREM2, SLCO2B1, GPR34, P2RY12, P2RY13, ENTPD1, BLNK, RAB3IL1, ADORA3, CRYBB1, GAL3ST4) that were consistently higher in both iPSC-derived and primary microglia (Table 1).

Figure 3C:
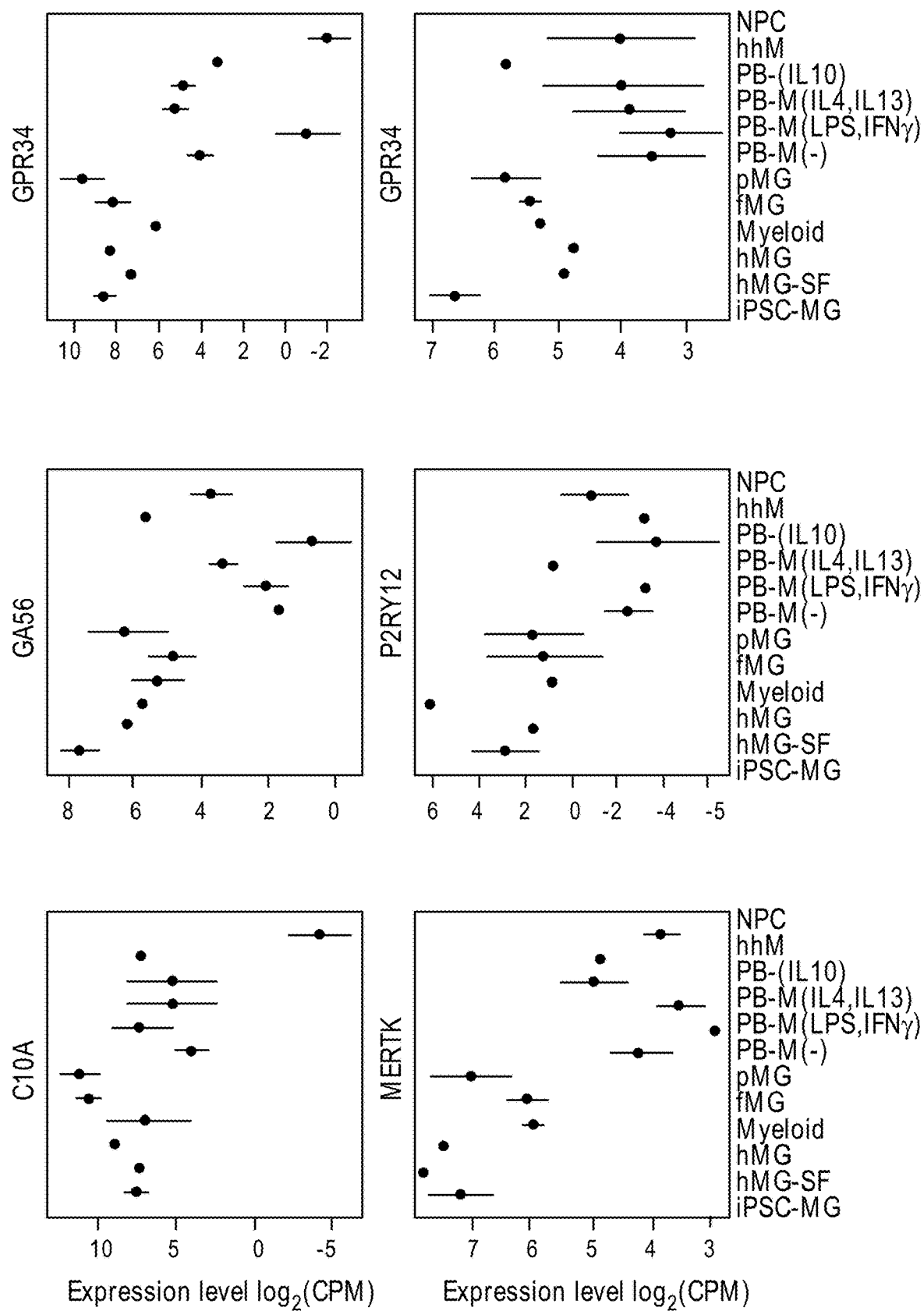

The study from Butovsky et al., proposed six genes, namely C1QA, GAS6, GPR34, MERTK, P2RY12 and PROS1 as unique signature in fetal and adult human primary microglia. Indeed, their high expression was consistent among all our microglial samples (iPSC-MG, hMG, hMG-SF) as well as in microglial samples from two independent studies (Muffat et al., 2016; Zhang et al., 2016) (FIG. 3C), whereas macrophages and neural progenitor cells (NPCs) showed lower levels (t-test: P<0.05 between microglia and macrophages or NPCs in all 6 genes). Table 2, which relates to FIG. 3C, shows the expression of the six human microglial validated signature genes in the microglial samples as determined by RNAseq. The values in Table 2 are log 2 transformed CPM.

TABLE 1

| | | iPSC-MG | hMG-SF | hhM | PB-M(−) | iPSC-MG/ hMG-SF | iPSC-MG/ hhM | iPSC-MG/ PB-M(−) |
|---|---|---|---|---|---|---|---|---|
| | TREM2 | 10.0 | 8.7 | 4.5 | 8.6 | 1.2 | 2.2 | 1.2 |
| | SLCO2B1 | 9.7 | 9.7 | 7.1 | 6.4 | 1.0 | 1.4 | 1.5 |
| | HEXB | 9.6 | 9.1 | 8.5 | 9.3 | 1.0 | 1.1 | 1.0 |
| | GPR34 | 8.8 | 7.6 | 3.4 | 4.3 | 1.2 | 2.5 | 2.0 |
| Common in | OLFML3 | 3.4 | 5.7 | 6.9 | 1.6 | 0.6 | 0.5 | 2.2 |
| all 3 studies | SLC2A5 | 2.9 | 4.3 | 3.8 | 6.9 | 0.7 | 0.8 | 0.4 |
| | P2RY12 | 2.4 | 1.2 | −3.6 | −2.9 | 2.0 | −0.7 | −0.8 |
| | P2RY13 | 1.1 | 3.0 | −1.6 | −1.1 | 0.4 | −0.7 | −1.0 |
| | TMEM119 | −0.5 | 2.7 | 4.7 | −2.5 | −0.2 | −0.1 | 0.2 |
| | LIPH | −4.4 | −3.4 | −1.7 | −2.2 | 1.3 | 2.6 | 2.0 |
| | CTSD | 11.0 | 12.5 | 9.3 | 11.7 | 0.9 | 1.2 | 0.9 |
| | TGFBR1 | 9.2 | 7.4 | 9.7 | 7.6 | 1.2 | 1.0 | 1.2 |
| | ENTPD1 | 8.3 | 6.3 | 5.1 | 6.0 | 1.3 | 1.6 | 1.4 |
| | IL10RA | 8.2 | 7.0 | 7.6 | 8.5 | 1.2 | 1.1 | 1.0 |
| | LAIR1 | 7.2 | 8.4 | 7.2 | 8.0 | 0.9 | 1.0 | 0.9 |
| Butovsky & | CYSLTR1 | 5.6 | 1.4 | 0.7 | 1.7 | 3.8 | 7.6 | 3.3 |
| Bennett | BLNK | 4.8 | 4.8 | 0.5 | 2.5 | 1.0 | 9.7 | 2.0 |
| | RAB3IL1 | 4.8 | 4.7 | 2.8 | 3.0 | 1.0 | 1.7 | 1.6 |
| | GOLM1 | 4.5 | 3.8 | 6.8 | 3.5 | 1.2 | 0.7 | 1.3 |
| | PMEPA1 | 4.1 | 3.6 | 4.2 | 2.2 | 1.1 | 1.0 | 1.9 |
| | OPHN1 | 3.6 | 3.4 | 2.6 | 3.5 | 1.0 | 1.4 | 1.0 |
| | CCR5 | 3.6 | 6.1 | 4.7 | 5.5 | 0.6 | 0.8 | 0.6 |
| | F11R | 8.0 | 7.6 | 6.4 | 8.6 | 1.1 | 1.3 | 0.9 |
| | ADORA3 | 7.0 | 7.4 | 1.4 | 1.7 | 0.9 | 4.9 | 4.1 |
| | SPINT1 | 6.9 | 5.2 | 3.0 | 7.8 | 1.3 | 2.3 | 0.9 |
| Butovsky & | CCL4 | 5.0 | 6.5 | 8.0 | 1.7 | 0.8 | 0.6 | 2.9 |
| Hickman | CRYBB1 | 3.2 | 3.2 | 1.0 | −1.1 | 1.0 | 3.2 | −2.9 |
| | CX3CR1 | 0.8 | −5.7 | −1.2 | −3.1 | −0.1 | −0.6 | −0.2 |
| | ANG | 0.4 | 0.6 | 0.6 | 1.5 | 0.7 | 0.8 | 0.3 |
| | LAG3 | −2.4 | 0.2 | −2.0 | −1.6 | −11.1 | 1.2 | 1.4 |
| Hickman & | GAL3ST4 | 3.0 | 4.3 | 2.7 | −0.8 | 0.7 | 1.1 | −3.9 |
| Bennett | | | | | | | | |

TABLE 2

| | iPSC-MG1 | iPSC-MG2 | iPSC-MG3 | iPSC-MG4 | iPSC-MG5 | iPSC-MG6 | hMG-SF | hMG |
|---|---|---|---|---|---|---|---|---|
| C1QA | 9.2 | 8.5 | 9.1 | 9.5 | 7.9 | 7.9 | 8.6 | 10.2 |
| GAS6 | 7.0 | 6.0 | 7.6 | 7.0 | 6.7 | 6.2 | 5.4 | 5.0 |
| GPR34 | 9.2 | 8.5 | 9.1 | 8.9 | 8.2 | 8.0 | 7.6 | 8.5 |
| MERTK | 7.6 | 7.3 | 7.7 | 8.5 | 8.8 | 8.6 | 8.6 | 8.3 |
| P2RY12 | 4.2 | 0.4 | 3.0 | 3.2 | 0.9 | 1.6 | 1.2 | 5.7 |
| PROS1 | 6.2 | 6.4 | 6.8 | 6.8 | 6.0 | 5.7 | 4.7 | 4.5 |

Figure 3D:
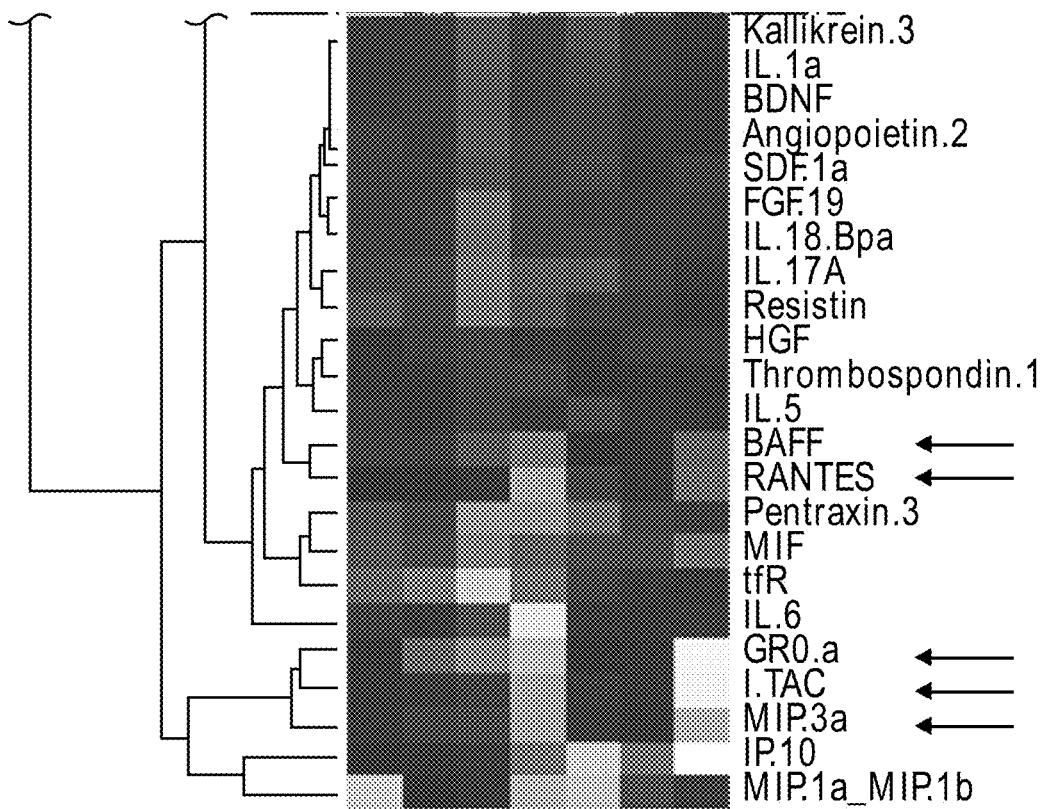
Figure 3D:
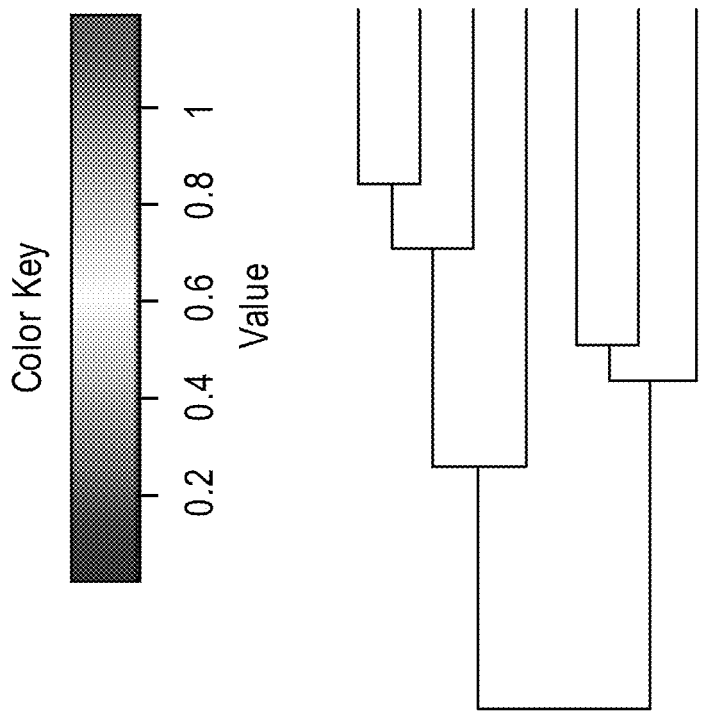
Figure 3D:
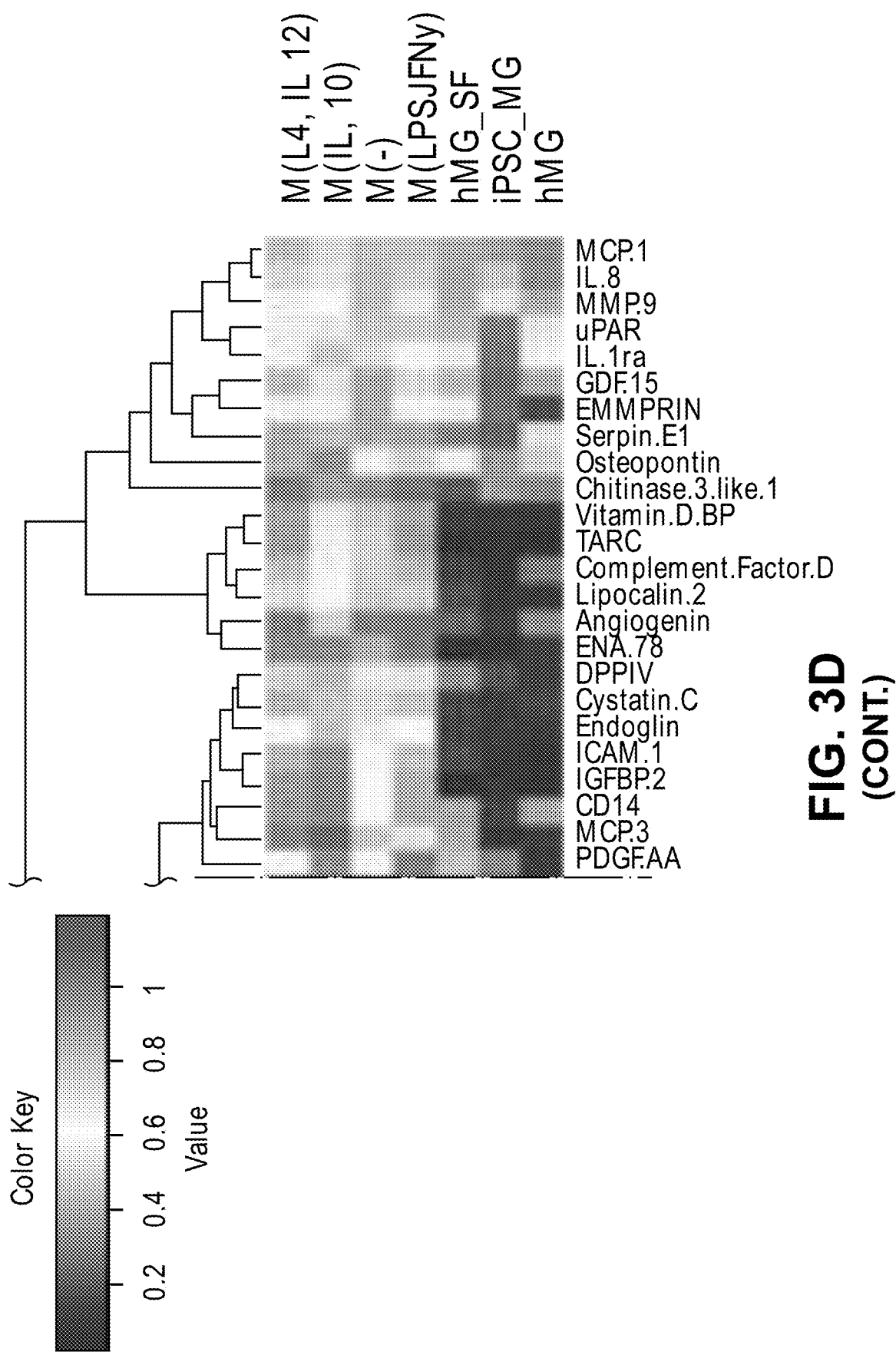

The cytokine profiles of human iPSC-derived and primary microglia were found to be similar, but to differ from those of peripheral blood derived macrophages. We analyzed proteins released by iPSC-MG, hMG, hMG-SF, and PB-M, including differentially polarized macrophages (FIG. 3D). Interestingly, similarities between iPSC-MG and primary microglia drastically increased when we replaced their culturing medium (containing serum, hMG) with our differentiation medium (hMG-SF), as the Pearson's correlation coefficient increased from R=0.473 to R=0.824. Of note, hMG showed upregulation of cytokines, such as RANTES, I-TAC, BAFF, GR0-a and MIP3a, which are typically released upon inflammation, and in fact, were also expressed by M(LPS,IFNγ) macrophages (arrows in FIG. 3D). Nevertheless, microglia samples clustered together and away from PB-M polarized as M(−), M(LPS,IFNγ), M(IL4,IL13) and M(IL10).

Figure 3E:
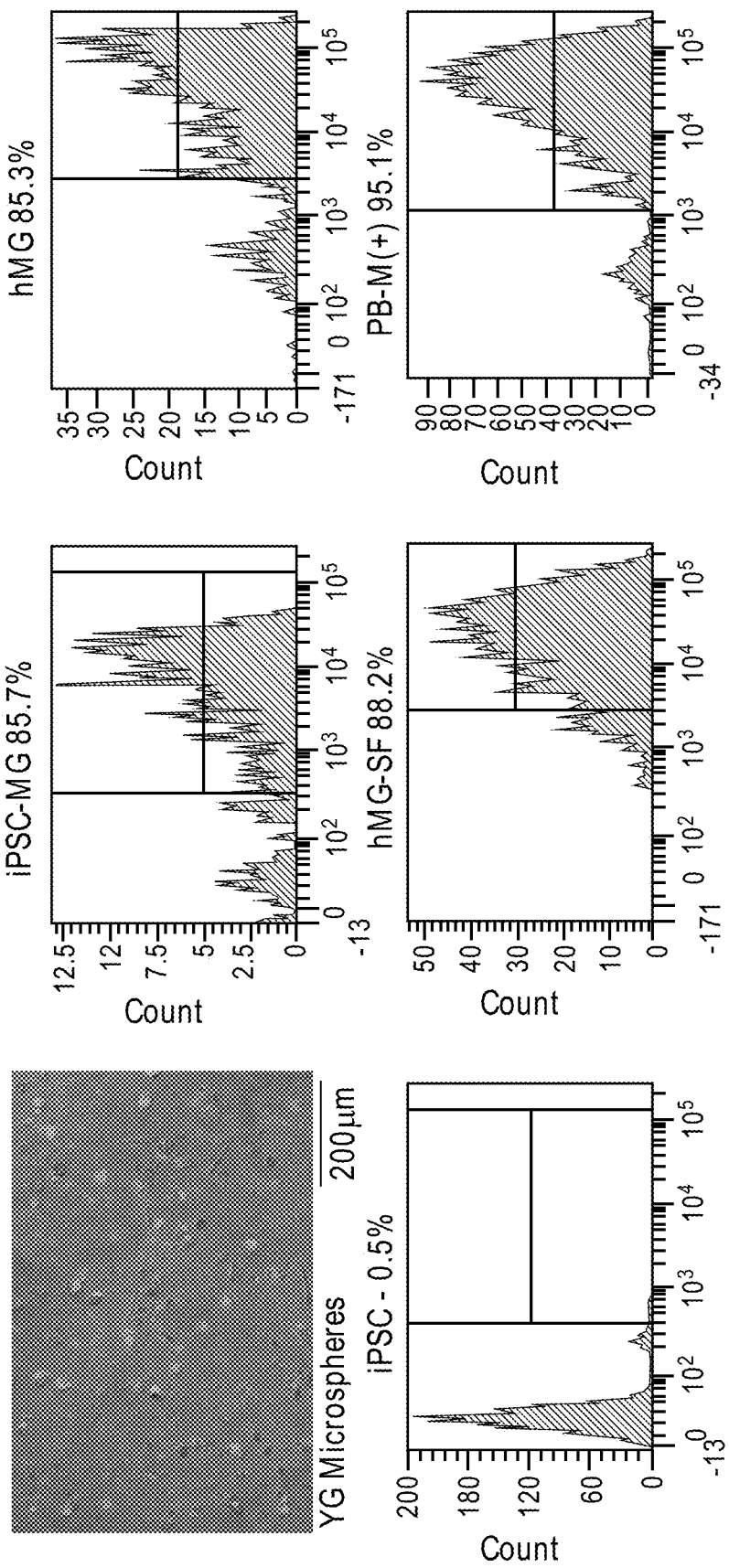

Our iPSC-MGs were also found to be functional phagocytes. iPSC-MG, hMG, hMG-SF, PB-M and undifferentiated iPSCs were challenged with a given amount of fluorescently labeled carboxylated latex microspheres per cell. Flow cytometry analysis showed that the majority of iPSC-MG were able to phagocytose (90±6%). These results were comparable to both hMG and hMG-SF. As expected, M(−) macrophages were also able to engulf microspheres while undifferentiated iPSCs were not (FIG. 3E).

Figure 4A:
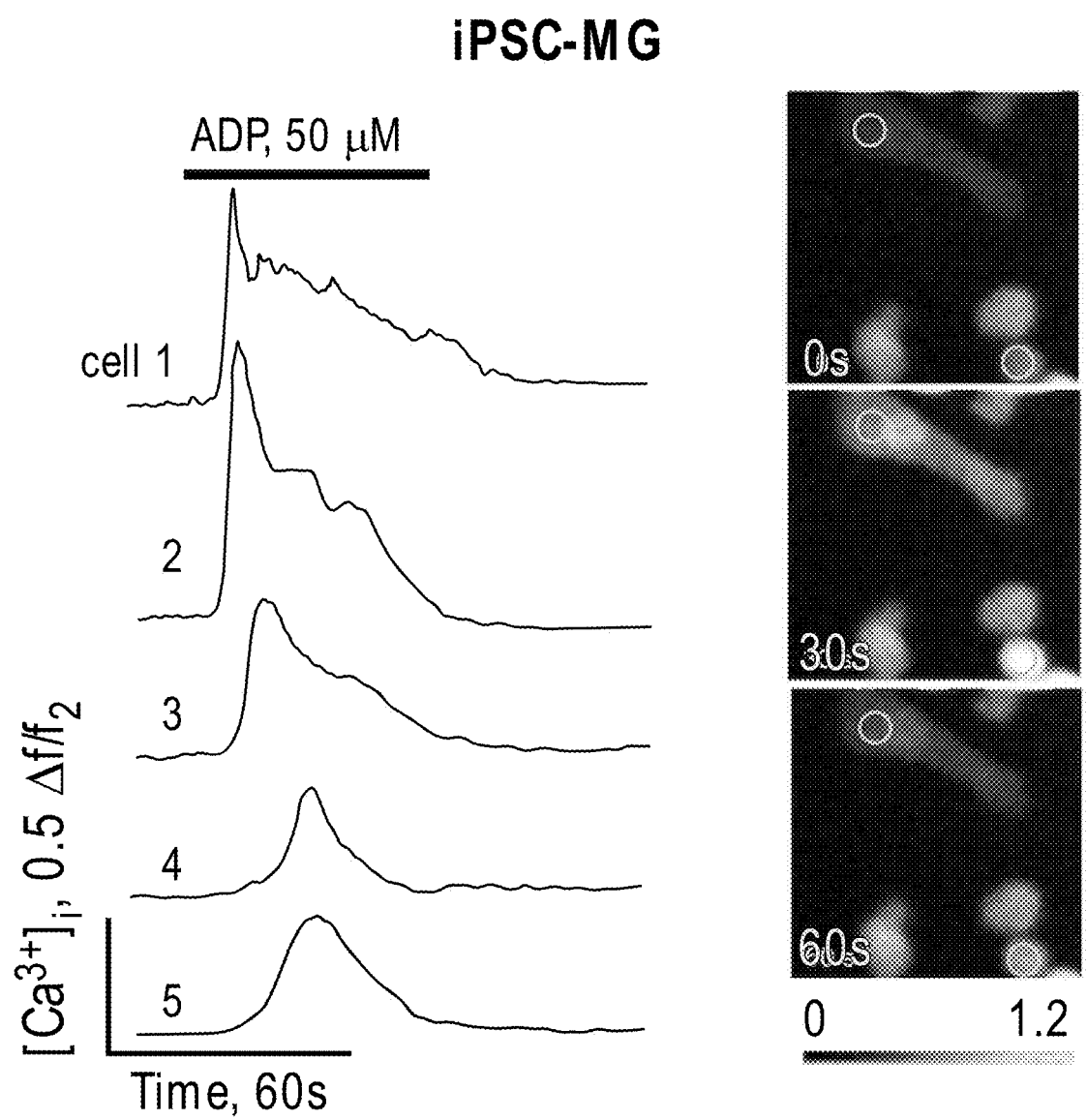
FIG. 4 A-F. ADP-evoked [Ca2+]i transients in microglia and macrophages. (A) Left panels show five example traces of intracellular Ca2+ transients following bath application of ADP in iPSC-MG loaded with the Ca2+ indicator Fluo-4/AM. Right panels show time lapse of changes in fluorescence intensity produced by ADP application. Traces originate from cells indicated by regions of interest in right panel. Bars represent duration of ADP or ATP application. (B-C) Same data as in A, obtained from primary human microglia (hMG) and hMG-SF correspondingly. (D) ADP and ATP responses in PB-M(-). Note the absence of significant [Ca2+]i transients in response to ADP in macrophages. (E) Statistical analysis for the amplitudes of [Ca2+]i transients. Maximum amplitude of [Ca2+]i transient for each responsive cell is presented as a dot in the corresponding category (***: $p<0.001$ by Student's t-test). (F) Percentages of ADP-responsive cells among all different cell types analyzed.
Figure 4B:
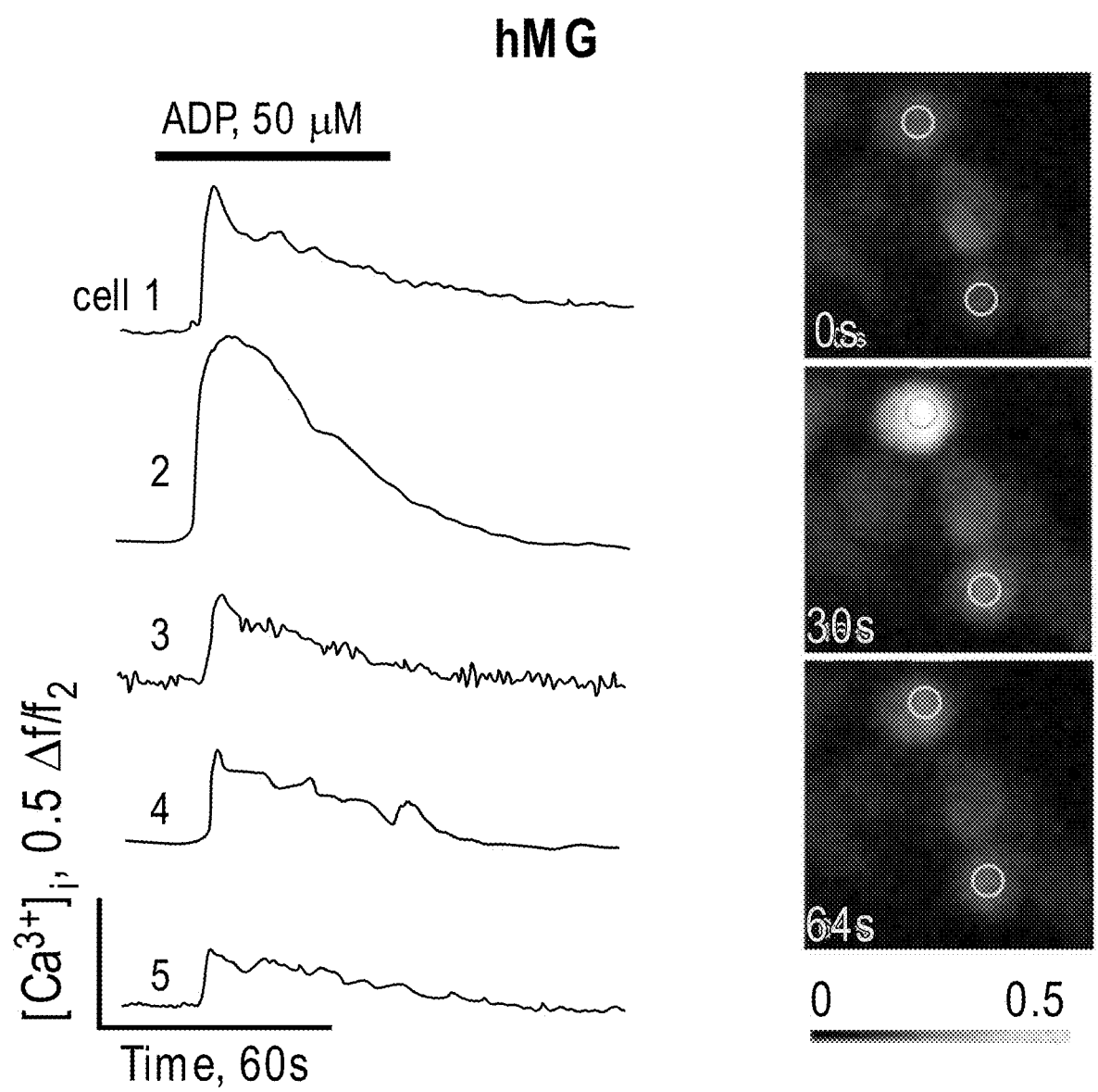
Figure 4C:
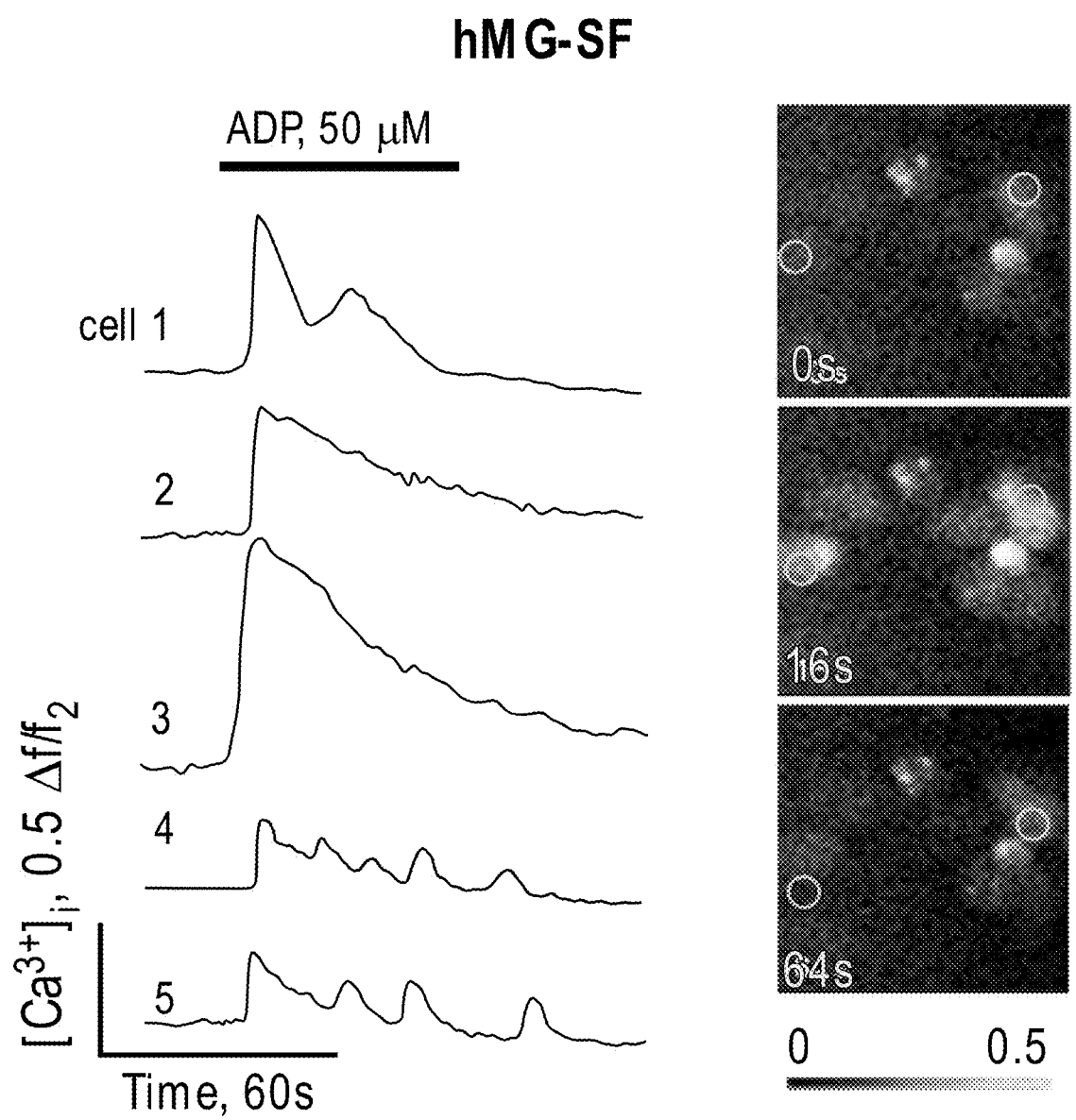
Figure 4D:
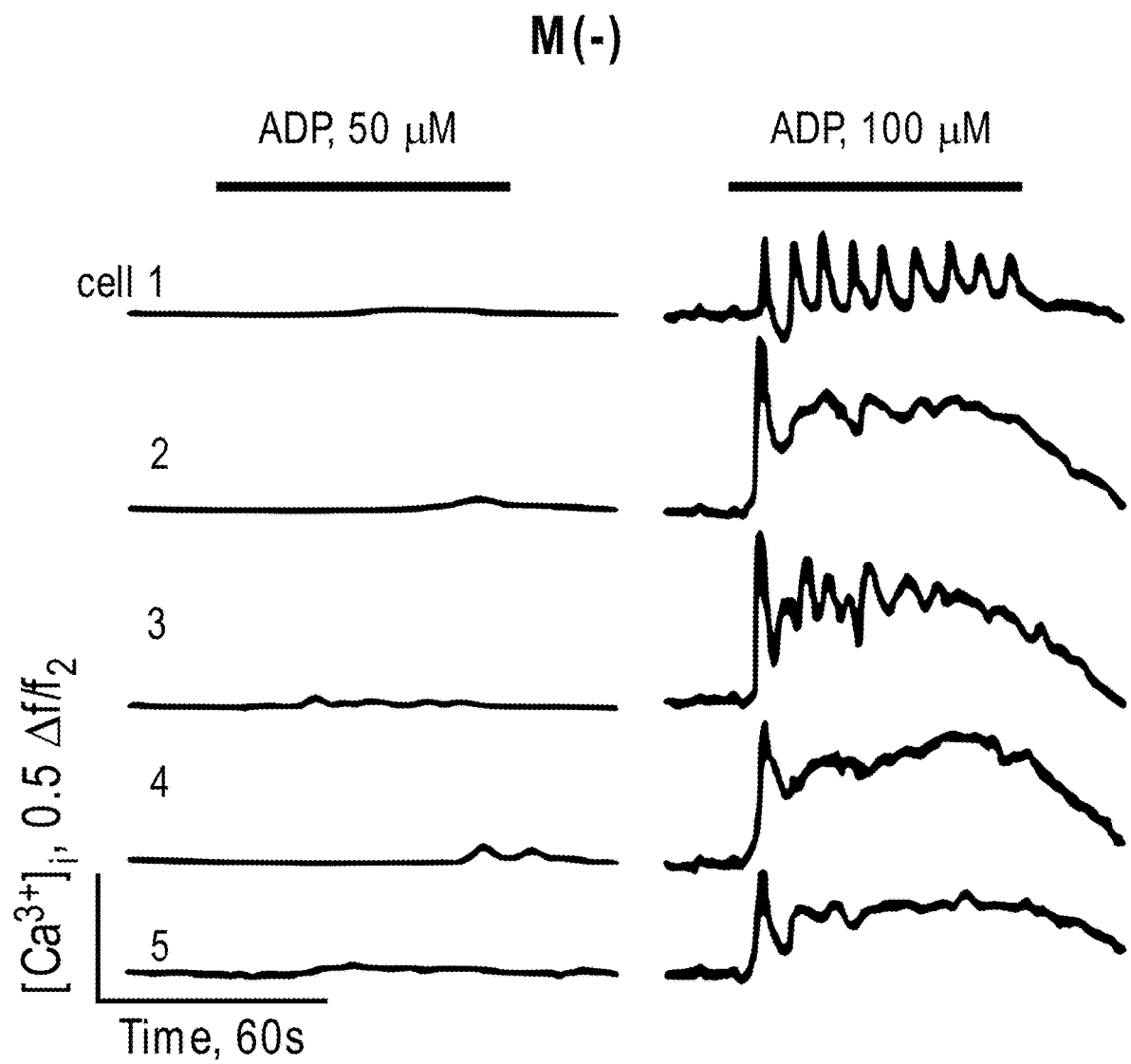
Figure 4E:
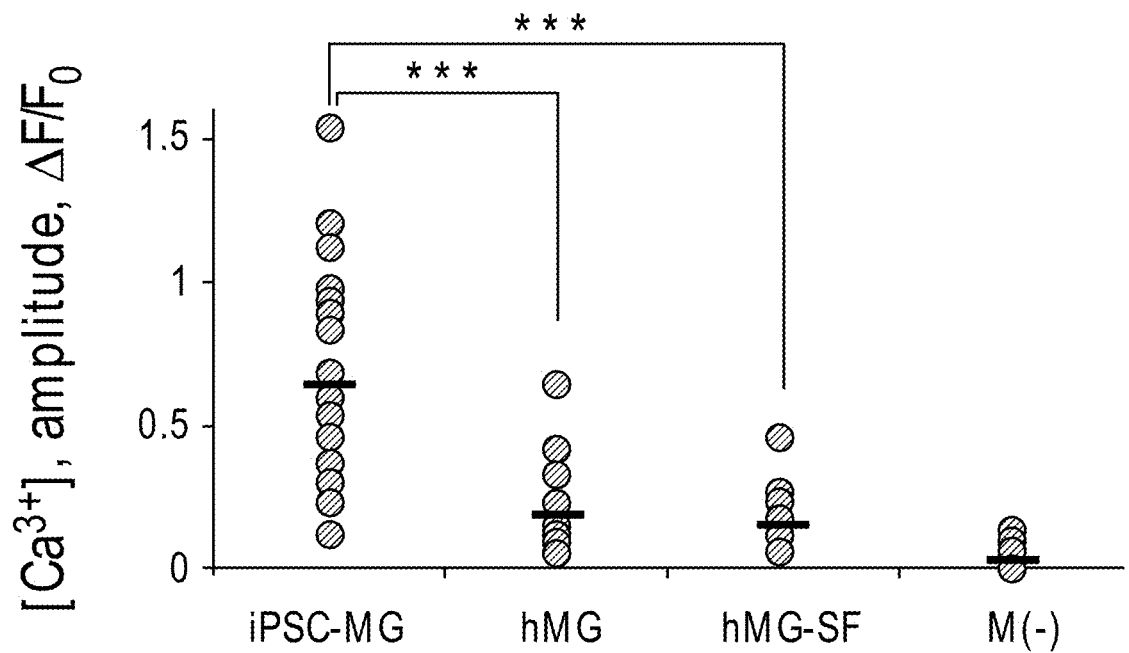
Figure 4F:
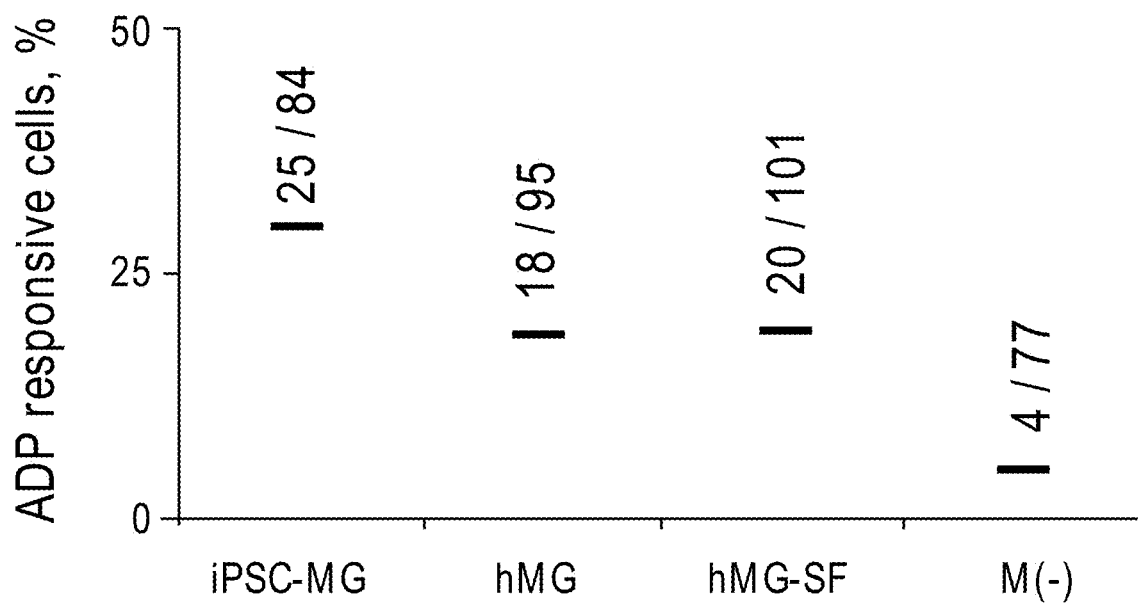

Our iPSC-MGs were also found to release intracellular $Ca2+$ in response to ADP. The microglial signature gene P2RY12 encodes a Gi protein-coupled purinergic receptor (Haynes et al., 2006) that responds to ADP resulting in intracellular $Ca2+$([$Ca2+$]i) transients, whereas PB-M do not express the receptor and consequently do not respond to ADP (Moore et al., 2015). Thus, ADP-induced [$Ca2+$]i transients are used to differentiate between microglia and macrophages. When we stimulated iPSC-MG, hMG, hMG-SF and PB-M with 50 µM ADP for 60 seconds, only microglial cells responded to ADP (FIG. 4A-C). The peak amplitude of ADP responses in iPSC-MG (FIG. 4E) as well as the number of responsive cells (FIG. 4F) were higher than either hMG or hMG-SF. None of the differentially polarized PB-M respond to ADP, but [$Ca2+$]i transients were reliably observed upon stimulation with 100 µM ATP (FIG. 4D and FIG. 8).

SUMMARY & DISCUSSION

In vitro hematopoietic differentiation of PSCs is equivalent to the in vivo primitive hematopoiesis rather than definitive hematopoiesis. This may explain why PSC-derived hematopoietic progenitors fail to produce long-term multi-lineage reconstitution (Vanhee et al., 2015). We hypothesized that PSC-derived myeloid progenitors might resemble primitive yolk sac myeloid progenitors, and therefore might give rise to microglia in vitro—as occurs during embryonic development. By stimulating PSCs with a myeloid inductive medium, we produced a KDR+CD235a+ primitive hemangioblast population and recapitulated the progression from CD45+CX3CR1− to CD45+CX3CR1+ microglial progenitors in vitro.

To ensure robustness and reproducibility of the protocol we tested a panel of 17 PSC lines, including iPSCs from MS, AD, PD patients or healthy individuals generated using different reprogramming strategies (e.g. mRNA/miRNA, Sendai virus). Fibroblasts were obtained from both male and female donors with ages ranging from 25 to 68. We were able to obtain microglial progenitors from all lines, with an average yield of 2-3 progenitors per undifferentiated PSC. As expected from such a diverse panel, the yield of progenitors varied across the lines, with no apparent correlation to a specific disease, reprogramming method or sex and age of the donor.

Our microglial progenitors gave rise to microglia that expressed typical markers, were ramified with highly motile processes capable of scanning the microenvironment, and were are able to phagocytose with an efficiency equivalent to that of normal human microglia.

While a definition of human microglial identity is not well established, recent genome-wide studies in mouse have provided datasets to facilitate the distinction of microglia from other myeloid or CNS cell types (Bennett et al., 2016; Butovsky et al., 2014; Hickman et al., 2013). Therefore, we compared the global mRNA expression of iPSC-MG to that of primary microglia and both peripheral blood-derived and hepatic macrophages to evaluate the proposed "signature genes" in human microglia. We included samples with different genetic backgrounds. Our analyses clearly showed that iPSC-MG clustered away from both circulating and other tissue-specific macrophages and clustered together with primary microglia cells and CD45+ cells (called "myeloid"), isolated from human brain extracts (Zhang et al., 2016). Furthermore our iPSC-MG expressed six genes suggested as being unique to human microglia (Butovsky et al., 2014), in addition to many other genes that are enriched in mouse microglia (Table 1).

The cytokines released by iPSC-MG were found to have similar profiles to those of hMG but distinct from those of PB-M—independent of their polarization status. Of note, hMG clustered more tightly with iPSC-MG when cultured in our medium (hMG-SF). Without wishing to be bound by theory, we hypothesize that the reason is the presence of serum in the hMG culture medium. In vivo, microglia reside "behind" the blood-brain barrier, and the presence of serum components triggers their activation (Ransohoff and Perry, 2009). Indeed, hMG cultured in serum showed increased levels of inflammatory molecules such as RANTES, GR0-A, I-TAC, BAFF and MIP3a, similarly to M(LPS,IFNγ) pro-inflammatory macrophages.

We also showed that iPSC-MG express a functional P2RY12 receptor at both transcript and protein levels. This receptor distinguishes rodent and human microglia from other myeloid cells (Butovsky et al., 2014) and its activation via ADP results in [$Ca2+$]i transients (Moore et al., 2015).

All microglia cells (iPSC-MG, hMG and hMG-SF) showed ADP-evoked [Ca2+]i transients, while PB-M were unresponsive to ADP but showed [Ca2+]i transients upon exposure to ATP, indicating that they were healthy and functional.

Figure 7:
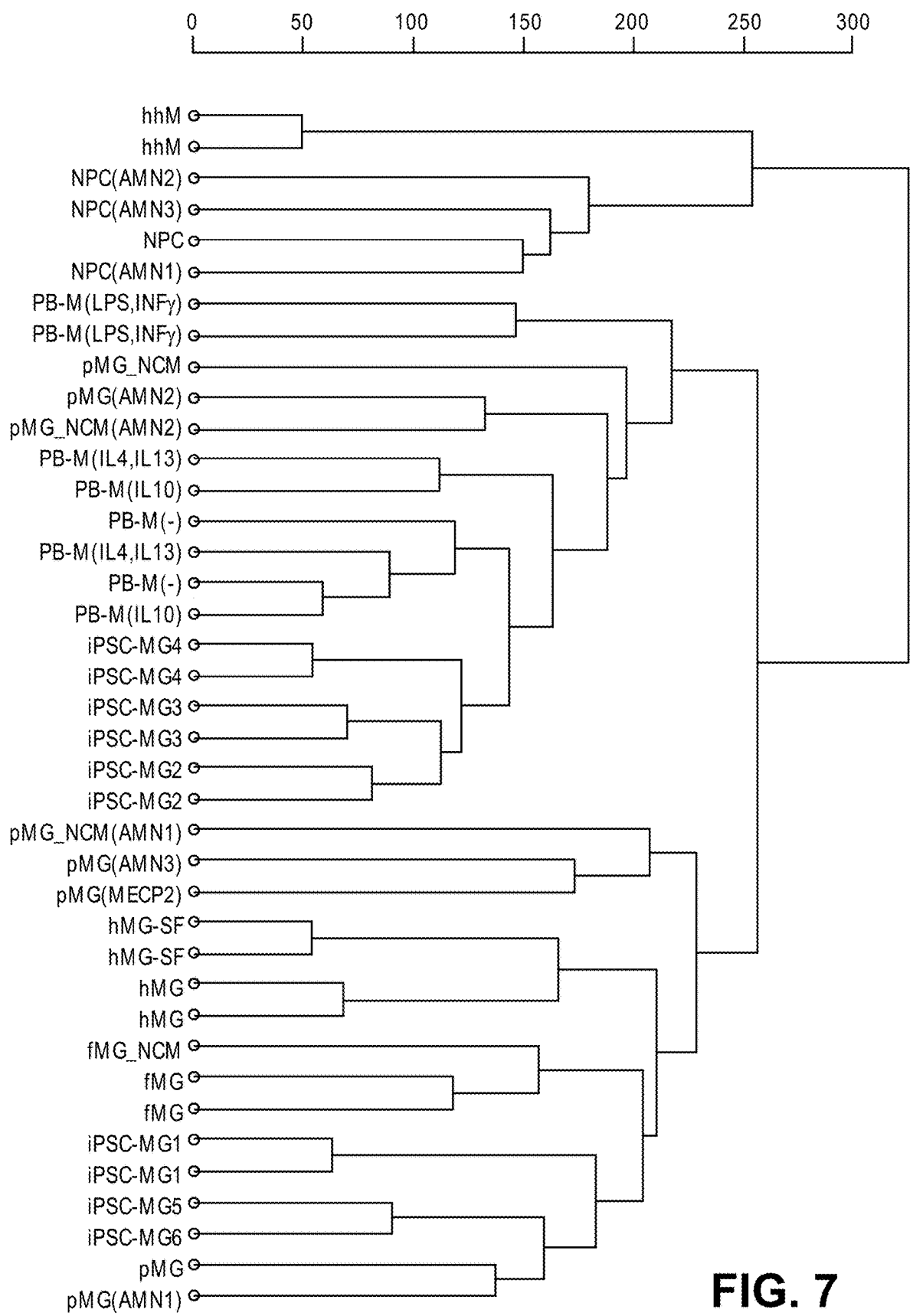
FIG. 7. Dendrogram showing hierarchical clustering of our RNA sequencing data with data obtained from an independent study (Muffat et al., 2016) on iPSC-derived microglia. Samples termed, or including the terms, fMG, pMG and/or NPC correspond to those samples from Muffat et al., 2016. Analysis is based on global RNA expression after batch correction.
Figure 8A:
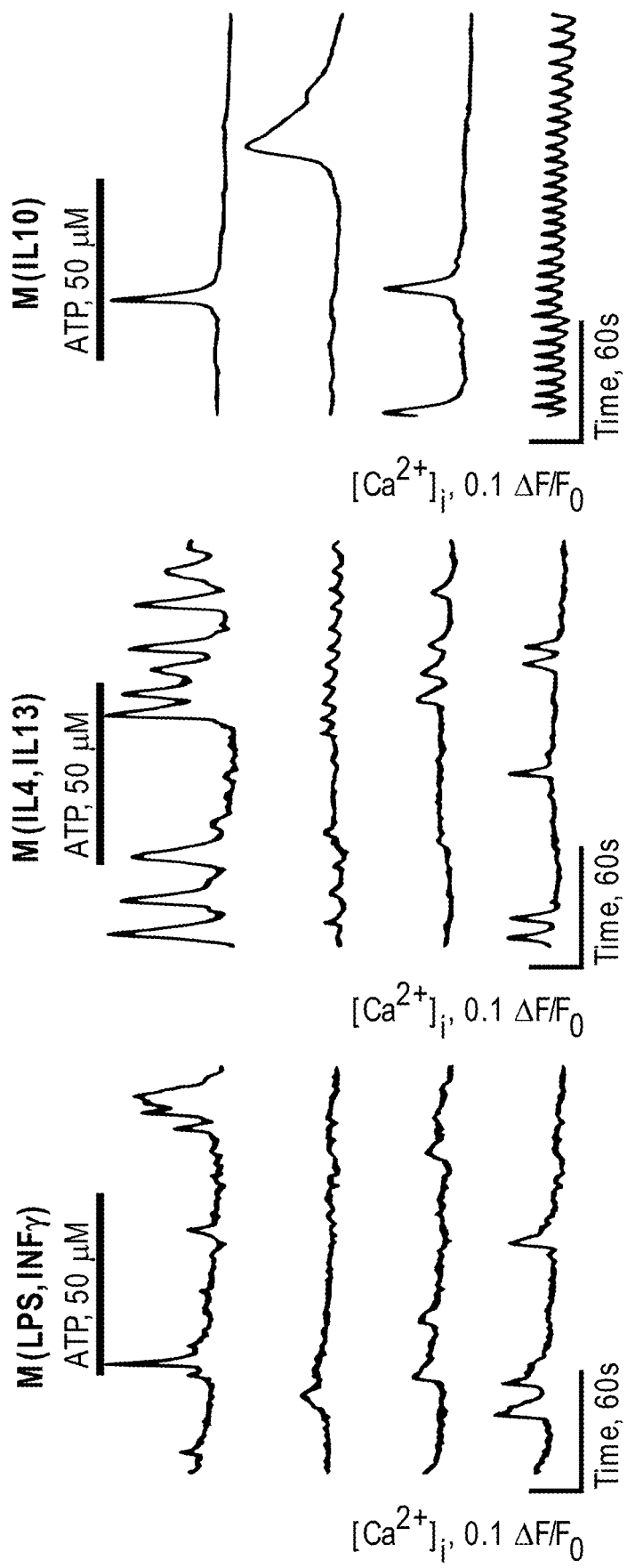
FIGS. 8 A-D. Intracellular Ca2+ transients in human peripheral blood macrophages. Four example traces of intracellular Ca2+ changes during (A) ADP or (B) ATP application in macrophages polarized with (LPS,INFγ), (IL4,IL13) and (IL10). Bars represent duration of ADP (in A) or ATP (in B) application. Statistical analysis for the amplitudes of [Ca2+]i transients of (C) ATP-responsive or (D) ADP-responsive macrophages. Maximum amplitude of [Ca2+]i transient for each responsive cell is presented as a dot.
Figure 8B:
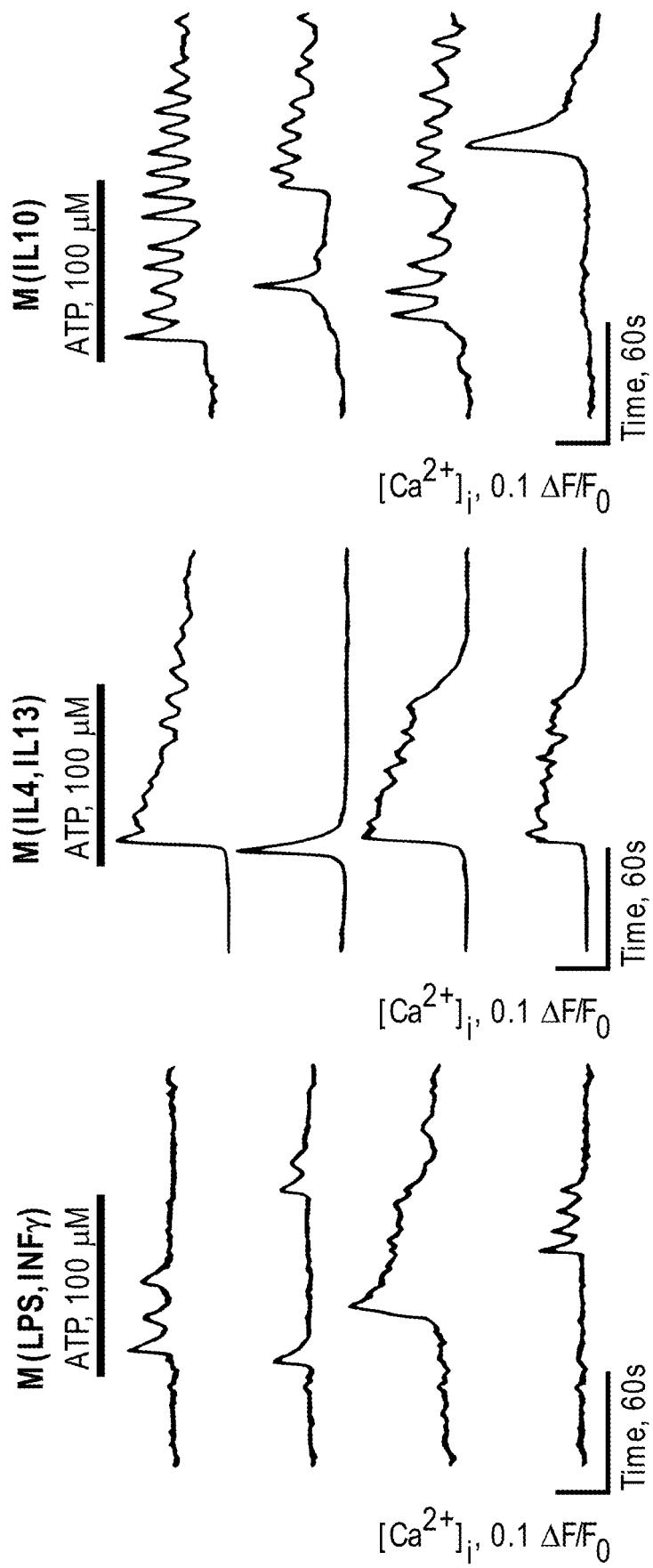
Figure 8C:
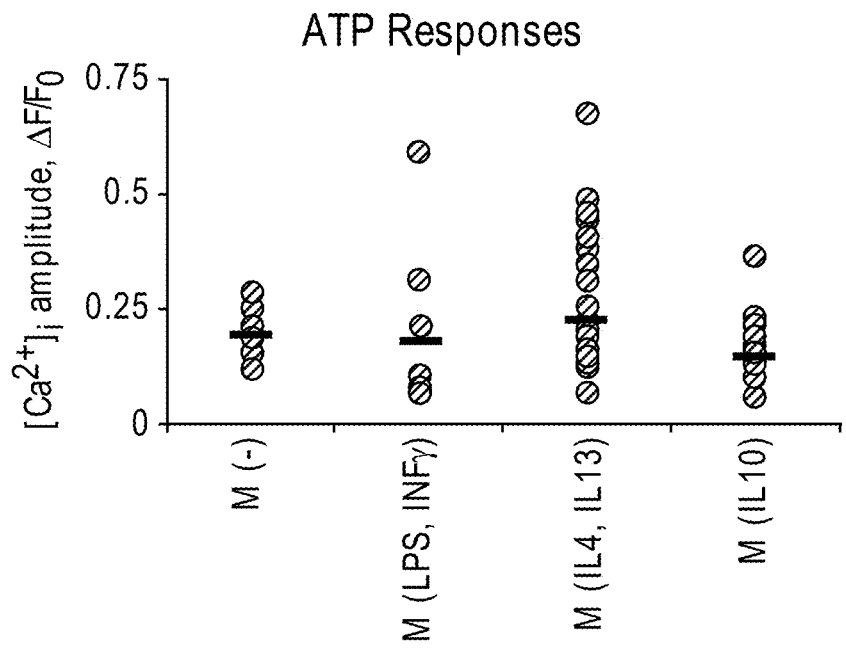
Figure 8D:
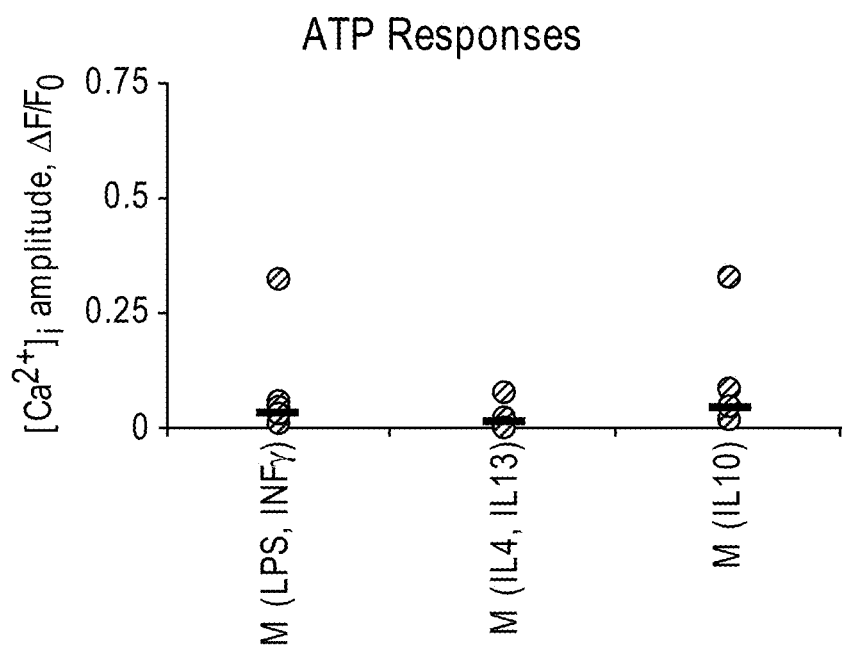

While protocols to differentiate mouse ESCs into microglia are known (see, for example, Beutner et al., 2010; Napoli et al., 2009; Tsuchiya et al., 2005) we found that such protocols are not effective with human iPSCs (data not shown)—underscoring the difference between the rodent and human systems. Human microglia-like cells have previously been trans-differentiated from peripheral blood (PB) monocytes, albeit without an extensive characterization of the microglia signature genes and functional studies (Etemad et al., 2012; Ohgidani et al., 2014). Muffat et al. (September 2016) described a human microglial differentiation protocol. We used RNAseq to compare microglia generated by our methods to microglia generated using the methods of Muffat et al. This comparative data is provided herein (FIG. 3C and FIG. 7). Both approaches mimic embryonic development of microglia, which are derived through a yolk sac progenitor defined as CD235a+. Both protocols use IL34 as the main driver to microglial lineage commitment and maturation in chemically defined media, and they both generate microglia with motile processes that express typical makers and are able to perform phagocytosis. Our strategy, based on monolayer cultures instead of embryoid bodies (EBs) formation, is comparable in efficiency but requires a smaller number of starting PSCs. Importantly, our protocol does not require the manual selection of specific EB morphology. We isolate microglial progenitors via FACS or magnetic beads, enabling high-throughput applications such as compound and genetic screens.

In summary, the new protocols described herein provide iPSC-MG as a new source of human microglia cells, which will complement studies in mouse models to better understand the role of microglia in health and disease. The protocols described herein are highly reproducible, whether performed with lines from healthy subjects or diseased patients, and thus provide a valuable tool to investigate pathogenic mechanisms of microglia dysfunction in neurological disorders. Furthermore, the inclusion of microglia in co-culture or three-dimensional systems, for example those involving neurons and other glial cell types, should facilitate in vitro disease-modeling to better recapitulate the complexity of the in vivo environment.

Example 2—Experimental Procedures

This Example provides details regarding the materials and methods used to perform the studies outlined in Example 1.

Pluripotent Stem Cell Lines

Two human ESC lines (RUES1 and H9, both NIH approved) and 15 iPSC lines were used in this study; these lines are described in the Supplemental Information. One iPSC line was a gift from Dr. Ricardo Feldman and all other iPSC lines were reprogrammed at the NYSCF Research Institute. Human primary microglia and hepatic macrophages were purchased from ScienCell Research Laboratories.

Microglial Differentiation Protocol

PSCs differentiation was induced with mTeSR Custom medium (StemCell Technologies), containing 80 ng/ml BMP4. At day 4 cells were induced with 25 ng/ml bFGF, 100 ng/ml SCF and 80 ng/ml VEGF in StemPro-34 SFM (with 2 mM GutaMAX, Life Technologies). Two days later, the medium was supplemented with 50 ng/ml SCF, 50 ng/ml IL-3, 5 ng/ml TPO, 50 ng/ml M-CSF and 50 ng/ml Flt3 and from day 14 with 50 ng/ml M-CSF, 50 ng/ml Flt3 and 25 ng/ml GM-CSF. Between days 25-50 CD14+ or CD14+ CX3CR1+ progenitors were isolated and re-plated onto tissue culture-treated dishes or Thermanox plastic coverslips (all from Thermo Scientific) in Microglial Medium (RPMI-1640, Life Technologies, with 2 mM GlutaMAX-I, 10 ng/ml GM-CSF and 100 ng/ml IL-34). Medium was replenished every 3 to 4 days for at least 2 weeks.

Tissue Culture & Cell Lines

All incubations were performed in a 37° C. incubator with 5% CO2 and all growth factors are human recombinant proteins purchased from R&D Systems, unless otherwise stated. All media contain 1× Penicillin/Streptomycin (P/S) or 1× Antibiotic-Antimycotic (Life Technologies). RT: room temperature.

RUES1 and H9 are NIH approved human ESC lines. All iPSC lines were derived from skin biopsies of de-identified donors upon specific institutional review board approvals and informed consent. The control iPSC lines 050643-01-MR-28495 (25 y.o. male), 050652-01-MR-28650 (45 y.o. female), 050598-01-MR-49026 (53 y.o. male), 050598-01-MR-025 (53 y.o. male), 051024-01-MR-005 (29 y.o. male), 050689-01-MR-012 (27 y.o. male), 050675-01-MR-012 (34 y.o. male), 050642-01-MR-001 (69 y.o. male), the PD line 050412-01-MR-49025 (63 y.o. male) and the AD line 050948-01-MR-028 (40 y.o. female) were reprogrammed using New York Stem Cell Foundation's high-throughput automated system (see U.S. Patent Application Publication No. 2013/0345094 and Paull et al., 2015) with the mRNA/miRNA method (StemGent) (Paull et al., 2015). iPSC102 (56 y.o. male) was reprogrammed manually from a multiple sclerosis patient, using mRNA/miRNA (Douvaras et al., 2014). 10001.198.01SV4Mut and 10001.198.01SV5Mut are two distinct clones reprogrammed with Sendai virus from a PD patient (68 y.o. male) with a GBA N370S mutation (Woodard et al., 2014) whereas 10001.198.01SV5WT is a CRISPR/Cas9 corrected line. MJ2136 was a kind gift from Dr. Ricardo Feldman and was reprogrammed with Sendai virus from a healthy control (Panicker et al., 2014).

The human primary microglia and hepatic macrophages were purchased from ScienCell along with Microglia Medium and Macrophage Medium (ScienCell).

PSC lines were cultured and expanded onto Matrigel-coated dishes in mTeSR1 medium (StemCell Technologies). Lines were passaged every 3-4 days using enzymatic detachment with Stempro Accutase (Life Technologies) for 5 min and re-plated in mTeSR1 medium with 10 µM Rock Inhibitor (Y2732, Stemgent) for 24 hours.

Isolation of Myeloid Progenitors

Cells from the supernatant fraction of the cultures were incubated with CX3CR1 and/or CD14 conjugated primary antibodies (see Table 3) or their respective isotype controls for 40 min on ice. Cells were then washed in FACS buffer (PBS, 0.5% BSA, 2 mM EDTA, 20 mM Glucose), pelleted at 300 g for 6 min and re-suspended in FACS buffer containing DAPI for dead cell exclusion. CD14+ or CD14+ CX3CR1+ cells were isolated via FACS on an ARIA-IIu™ Cell Sorter (BD Biosciences) using the 100 µm ceramic nozzle, and 20 psi.

Freezing and Thawing of the Myeloid Progenitors

Myeloid progenitor cells were frozen after isolation in cryogenic vials (Thermo Scientific) in freezing medium consisting of 90% FBS (Life Technologies) and 10% DMSO (Sigma-Aldrich). Cells were then transferred into a Mr.Frosty (Thermo Scientific) container and placed overnight at −80° C. The next day, cryogenic vials were transferred to liquid nitrogen for long-term storage.

To thaw the cells, the cryogenic vial was transferred in a 37° C. water bath for 1-2 min, until partially thawed. Under a laminar flow hood, RPMI-1640 medium was added to 5× the original volume of the vial. Cell were then centrifuged at 300 g for 6 min, resuspended in the appropriate amount of medium and plated onto tissue culture treated plastic.

Detailed Microglial Differentiation Protocol

PSCs were plated onto Matrigel (BD Biosciences) in a 15×103 cells/cm2 density in mTeSR1 medium containing 10 μM Rock Inhibitor for 24 hours. When individual colonies were visible (usually 2-4 days after plating), differentiation was induced by providing mTeSR Custom medium (StemCell Technologies), containing 80 ng/ml BMP4. mTeSR Custom medium is mTeSR1 medium without Lithium Chloride, GABA, Pipecolic Acid, bFGF and TGFβ1 (Stem Cell Technologies). The medium was changed daily for 4 days, when cells were induced with StemPro-34 SFM (containing 2 mM GutaMAX-I, Life Technologies) supplemented with 25 ng/ml bFGF, 100 ng/ml SCF and 80 ng/ml VEGF. Two days later, the medium was switched to StemPro-34 containing 50 ng/ml SCF, 50 ng/ml IL-3, 5 ng/ml TPO, 50 ng/ml M-CSF and 50 ng/ml Flt3. On day 10, the supernatant fraction of the cultures was pelleted, resuspended in fresh medium (same as before) and returned to their dishes. On day 14, floating cells were pelleted, resuspended in StemPro-34 containing 50 ng/ml M-CSF, 50 ng/ml Flt3 and 25 ng/ml GM-CSF and replated back to their dishes. The procedure was repeated every four days. From day 24-52, a small amount of floating cells was processed for flow cytometry analysis to determine the peak of the CD14/CX3CR1 double positive progenitors. After the isolation of CD14+ or CD14+CX3CR1+ progenitors, cells were plated onto tissue culture-treated dishes or Thermanox plastic coverslips (all from Thermo Scientific) in a 40-50×103 cells/cm2 in SF-Microglial Medium (RPMI-1640 from Life Technologies supplemented with 2 mM GlutaMAX-I, 10 ng/ml GM-CSF and 100 ng/ml IL-34). Medium was replenished every 3 to 4 days for at least 2 weeks.

Peripheral Blood Derived Macrophages and Polarization

Macrophages were differentiated from isolated human mononuclear cells obtained from peripheral blood of healthy individuals at the New York Blood Center as previously described (Pallotta et al., 2015). Briefly, CD14+ cells were isolated after Ficoll gradient and magnetic beads based separation using the EasySep Human CD14 Positive Selection Kit (STEMCELL Technologies). Cells were then seeded in ultra-low attachment plates for 5 days in a 5×105 cells/ml density and differentiated to macrophages using RPMI-1640 supplemented with 2 mM GlutaMAX-I, 10% heat-inactivated human serum (Sigma-Aldrich) and 20 ng/ml M-CSF (PeproTech). For polarization, macrophages were kept in the same medium (M(−)), or treated with 100 ng/ml LPS (Sigma-Aldrich) and 100 ng/ml IFNγ(M(LPS, IFNγ)), 40 ng/ml IL-4 and 20 ng/ml IL-13 (M(IL4,IL13)) or 40 ng/ml IL-10 (M(IL10); all from PeproTech) macrophages.

Immunofluorescent Staining

Cells were washed 3× in PBS-T (PBS containing 0.1% Triton-X100) for 10 min, incubated for 2 hours in blocking serum (PBS-T with 5% donkey serum) and primary antibodies (see Table 3) were applied overnight at 4° C. The next day, cells were washed 3× in PBS-T for 15 min, incubated with secondary antibodies for 2 hours at room-temperature (RT), washed 3× for 10 min in PBS-T, counterstained with DAPI for 15 min at RT and washed 2× in PBS. Secondary antibodies were used at 1:500 dilution. Images were acquired using an Olympus IX71 inverted microscope, equipped with Olympus DP30BW black and white digital camera. Fluorescent colors were digitally applied using the Olympus software DP Manager or imageJ.

Flow Cytometry Analysis

Cells were enzymatically harvested by Accutase treatment for 5 min at 37° C. and then scrapped with a cell lifter (Sigma-Aldrich). Cells were then re-suspended in 100 μl of their respective medium containing the appropriate amount of fluorescence-conjugated antibodies (see Table 3) and were incubated on ice for 40 min shielded from light. Isotype controls or secondary antibodies only were used to measure the baseline background signal. DAPI or Sytox Green (Thermofisher) were used for dead cell exclusion. Analyses were performed on a five-laser BD Biosciences ARIA-IIu™ Cell Sorter or on a four-laser Attune NxT Flow Cytometer (ThermoFisher). Data were analyzed using BD FACSDiva™ software or FlowJo version 9.9.4 (FlowJo LLC).

TABLE 3

Antibodies used for flow cytometry and immunofluorescent analyses

| Name | Host | Vendor |
| --- | --- | --- |
| IBA1 | Rabbit | Wako |
| P2RY12 | Rabbit | Alomone Labs |
| CD11b-Alexa700 | Mouse | BD Pharmingen |
| CD11c-PE | Mouse | BD Pharmingen |
| CX3CR1-PE | Mouse | R&D Systems |
| CD14-APC | Mouse | BioRad |
| CD45-v450 | Mouse | BD Horizon |
| CD309-APC | Mouse | Miltenyi Biotec |
| CD235a-PE | Mouse | BD Pharmingen |
| anti-rabbit IgG-Alexa488 | Donkey | Life Technologies |
| anti-mouse IgG-Alexa555 | Donkey | Life Technologies |

Phagocytosis Assay

Phagocytosis assay was performed as previously described (Enomoto et al., 2013). Briefly, Fluoresbrite YG Carboxylate Microspheres 1.00 μm (Polysciences) were added to the dishes containing adherent microglial cells in a 200 microspheres/cell ratio. After incubating the cultures at 37° C. for 3 hours, fluorescent images were acquired with an Olympus IX71 inverted microscope, equipped with Olympus DP30BW black and white digital camera. Then cells were washed 3× with PBS, treated with Accutase for 5 min and completely detached using a cell lifter. After centrifuging, cells were resuspended in FACS buffer containing DAPI and analyzed on a BD Biosciences ARIA-IIu™ Cell Sorter.

Cytokine Profiler and Clustering

For analysis of the secreted cytokine profile of microglial cells, the Human XL Cytokine Array Kit of the Proteome Profiler Antibody Arrays (R&D Systems) was used according to the manufacturer's instructions. Supernatant was collected from the cultures and stored at −80° C. for up to 3 months. Membranes were directly visualized in a Kodak Image Station 4000MM PRO and images were acquired using the Carestream Molecular Imaging Software.

For analysis of the signals, images were imported to Image J and the Protein Array Analyzer plugin was used. The intensity reading of the two identical spots was then averaged and the mean value of 8 negative controls was subtracted from every value. Finally, data were expressed as intensity ratio compared to the mean intensity of the 6 reference spots (positive controls). Heatmap and clustering for the protein profiler analysis was generated using heatmap.2 in R version 3.3.1.

Intracellular Ca2+ Imaging

Cells were cultured onto Thermanox plastic coverslips (ThermoFisher) and were incubated for 30 min at 37° C. with medium supplemented with the fluorescent Ca2+ dye Fluo-4/AM (2□M) mixed at 1:1 with Pluronic-127 reagent (both from Invitrogen). Cells were subsequently washed twice with RPMI-1640 media containing 1% BSA (Life Technologies), 1× GlutaMAX-I and 10 mM HEPES (Sigma-Aldrich) pH adjusted to 7.5. Cells were allowed to recover for an additional 30 min to ensure dye esterification. Coverslips were then transferred to a recording chamber mounted onto an upright Olympus BX61 microscope. Fluorescence was recorded at 2 Hz by a cooled CCD camera (Hamamatsu Orca R2). Drug application was done via whole chamber perfusion at room temperature for a period of 60 s. $[Ca^{2+}]i$ transients are expressed in the form of $\Delta F(t)/F0$, where F0 is a baseline fluorescence of a given region of interest and $\Delta F$ is the difference between current level of fluorescence F(t) and F0. Fluctuations of $\Delta F(t)/F0$ that were less than 0.05 were considered as non-responses.

RNA Sequencing and Analyses

RNA isolation was performed using the RNeasy Plus Mini Kit (Qiagen) with QIAshredder (Qiagen). Cells were enzymatically detached after treatment with Accutase for 5 min and using a cell lifter. After centrifuging, cells were washed with PBS and resuspended in lysis buffer. Samples were then stored at −80° C. until processed further according to manufacturer's instructions. RNA was eluted in 30 μl RNase free ddH2O and quantified with a NanoDrop 8000 spectrophotometer (Thermo Scientific).

Single-ended RNAseq data were generated with the Illumina HiSeq 2500 platform following the Illumina protocol. The raw sequencing reads were aligned to human hg19 genome using star aligner (version 2.5.0b). Following read alignment, featureCounts (Liao et al., 2014) was used to quantify the gene expression at the gene level based on Ensembl gene model GRCh37.70. Genes with at least 1 count per million (CPM) in at least one sample were considered expressed and hence retained for further analysis, otherwise removed. The gene level read counts data were normalized using trimmed mean of M-values normalization (TMM) method (Robinson et al., 2010) to adjust for sequencing library size difference. Hierarchical cluster analysis based on transcriptome-wide gene expression was performed using R programming language.

For re-analysis of microglia RNAseq data from Zhang et al. (Zhang et al., 2016), we downloaded the raw RNAseq data of "myeloid" cells from gene expression omnibus (GEO: accession GSE73721). The RNAseq read data was processed using the same star/featureCounts pipeline as described above and then the gene level read counts were combined with the gene count data of our samples. The merged data were normalized with the TMM approach and then corrected for batch using linear regression. Hierarchical cluster analysis was used to illustrate the sample dissimilarity.

Similarly, for comparison with a recently published human iPSC-derived microglial dataset from Muffat et al., 2016, we downloaded their RNAseq read data from GEO (accession GSE85839) and then applied the same RNAseq analysis pipeline to obtain gene level count data which was merged with the read count of the present samples. The merged data was normalized and batch corrected before carrying out hierarchical cluster analysis.

Statistics

Frequencies were calculated in excel and expressed as Mean±Standard Error of the Mean (SEM). Statistical analysis of $[Ca2+]i$ transients amplitude was performed using unpaired Student's t-test to compare mean values in excel. The P value significance of the cluster partition for the dendrogram based on the six signature genes was estimated as the fraction of 1000 repeated permutations (shuffling gene expression values within each gene) in which the cluster center distance obtained from k-means cluster with two centers was more extreme than that in the original data. Pearson's correlation coefficient between iPSC-MG and hMG or hMG-SF for cytokine release data was calculated using GraphPad Prism 6.

Example 3

Alternative Protocols for the Generation of Microglia from Pluripotent Stem Cells This example provides alternative exemplary protocols for the generation of microglia from pluripotent stem cells. In these protocols, CD14+/CX3CR1+ microglial progenitors are isolated via FACS, or based on only CD14 expression using magnetic bead-based isolation, and the isolated CD14+ progenitors are then plated onto tissue culture treated plastic in either an alternative ("A") microglial differentiation medium (comprising M-CSF, GM-CSF, NGF-β and CCL2), or in a regular ("R") microglial differentiation medium (comprising GM-CSF and IL-34, as used in the Examples 1 and 2). Except where stated otherwise, the materials and methods for this Example are the same as those described above for Examples 1 and 2.

In one exemplary protocol, the following steps are performed on the indicated days:

Day 0: Induce undifferentiated iPSC colonies grown onto Matrigel (roughly 1 mm in diameter) by switching to mTSeR Custom supplemented with 80 ng/ml BMP4. Change media every day.

Day 4: Switch media to StemPro-34 with 2 mM Glutamax, 25 ng/ml bFGF, 100 ng/ml SCF and 80 ng/ml VEGF.

Day 6: Switch media to StemPro-34 with 2 mM Glutamax, 50 ng/ml SCF, 50 ng/ml IL-3, 5 ng/ml TPO, 50 ng/ml M-CSF, 50 ng/ml Flt-3.

Day 10: Collect the cells from the supernatant, spin-down and re-suspend in StemPro-34 with 2 mM Glutamax, 50 ng/ml SCF, 50 ng/ml IL-3, 5 ng/ml TPO, 50 ng/ml M-CSF, 50 ng/ml Flt-3. Put the cells back into their well.

Day 14: Collect the cells from the supernatant, spin-down and re-suspend in StemPro-34 with 2 mM Glutamax, 50 ng/ml M-CSF, 50 ng/ml Flt-3, 25 ng/ml GM-CSF. Put the cells back into their well. Repeat every four days.

Day 24-52: FACS sort or use magnetic beads isolation for CD14+ cells. CD14+ cells are frozen in ProFreeze or 50% FBS/10% DMSO with 60% viability. The CD14+ progenitors are used in the following differentiation step to produce microglial cells.

Following the above step, plate the CD14+ progenitor cells at a density of 50K-100K cells/cm2 on tissue culture treated plastic. Feed the cells with: either the alternative "A" media (i.e. RPMI-1640 supplemented with 2 mM Glutamax, 10 ng/ml M-CSF, 10 ng/ml GM-CSF, 10 ng/ml NGF-β and 100 ng/ml CCL-2), or the regular "R" media (i.e. RPMI-1640 supplemented with 2 mM Glutamax, 10 ng/ml GM-CSF and 100 ng/ml IL-34). If media "A" is used, change medium every other day for 2 weeks. If media "R" is used, change the medium every four days for 2 weeks. This step will produce microglial cells from the CD14+ progenitor cells.

It is not essential to isolate the CD14+ cells (using FACS or magnetic beads) prior to performing the microglial differentiation step. For example, in some embodiments, instead of isolating CD14+ cells, all of the cells in the supernatant are used for the subsequent microglial differentiation step. In addition, one of skill in the art will recognize that certain modifications of these exemplary protocols (e.g. variations in the concentrations of agents and timing of media changes, etc.) can be used and are within the scope of the present invention.

Figure 9:
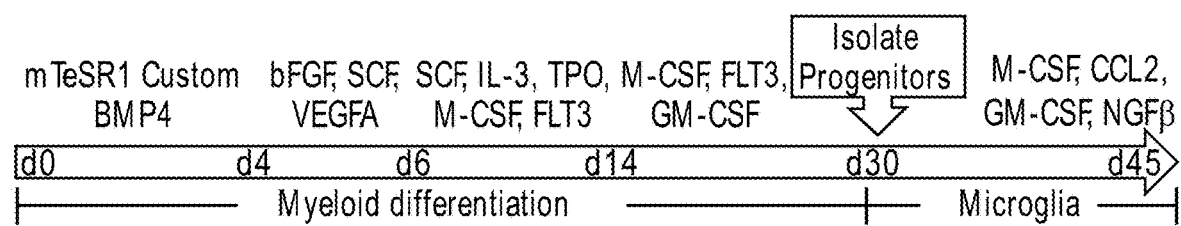
FIG. 9. Schematic illustration of an exemplary protocol for generation of microglia from pluripotent stem cells, in which the "alternative" or "A" medium (described in Example 3) is used for the final microglial differentiation step.
Figure 10:
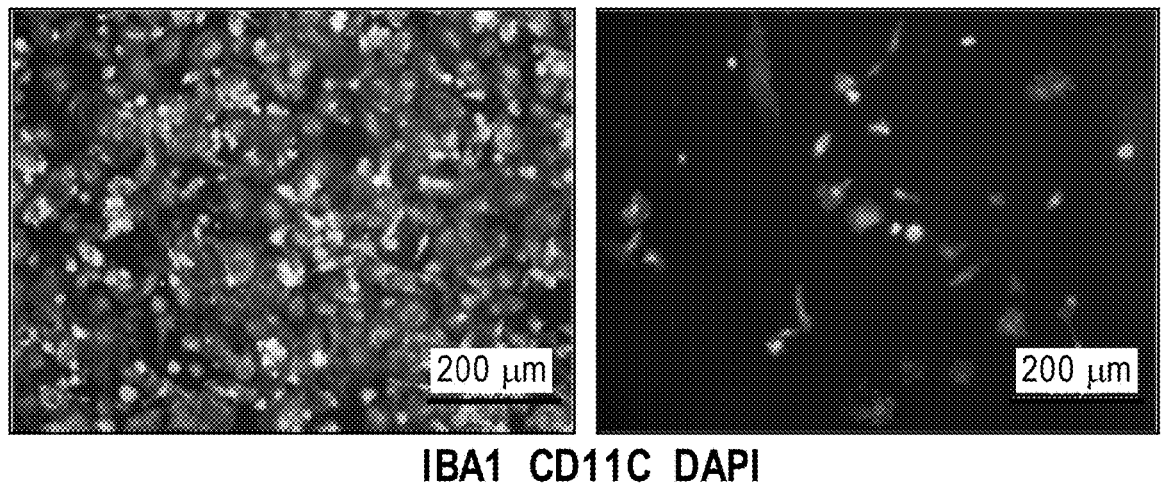
FIG. 10. Results of immunofluorescence staining of microglial cells differentiated from microglial precursors using the "alternative" or "A" medium described in Example 3. Staining for IBA1 and CD11c is shown. Nuclei are stained with DAPI. The left and right panels are images from different experiments where different lines and different seeding densities of cells were used.

FIG. 9 provides a schematic illustration of such an exemplary protocol in which the alternative "A" medium is used for the final microglial differentiation step. The cells produced using the alternative "A" medium for the final differentiation step express the microglial markers IBA1 and CD11c (as determined by immunofluorescence-staining; see FIG. 10) as well as CD11b, CD11c, CX3CR1, P2RY12, CD45 (as determined by FACs).

Studies were performed to test the effects of using the "A" versus "R" microglial differentiation medium, and also to test the effects of using various different substrates for plating of the microglial progenitors. Table 4 below shows the percentage (%) of total cells that expressed the indicated markers when the microglial progenitors were plated on the indicated substrates (i.e. plastic, laminin, fibrobectin or matrigel) and when cultured in either the "A" or "R" media. The microglial progenitors can be plated on any suitable substrate, including any of the substrates shown and tested below. In some embodiments, including, but not limited to, those where adherent cells are desired (e.g. for performing immunofluorescence studies) plastic is used. In some embodiments, including, but not limited to, those where cell adhesion is not required, Matrigel is used.

TABLE 4

Effects of Differentiation Media and Substrate on Microglial Marker Profiles

| | CD11b | CD11c | CX3CR1 | P2RY12 | CD14 | CD45 |
|---|---|---|---|---|---|---|
| Plastic-A | 85 | 89.9 | 15.2 | 14.9 | 51 | 99.9 |
| Plastic-R | 89.6 | 86.9 | 23.1 | 12.4 | 54.9 | 99.7 |
| Laminin-A | 72.6 | 86.5 | 30 | 27.9 | 67 | 99.8 |
| Laminin-R | 80 | 89 | 38.1 | 35 | 72.6 | 99.7 |
| Fibronectin-A | 77.1 | 90 | 38.8 | 29.7 | 76.6 | 99.9 |
| Fibronectin-R | 86 | 80.8 | 20 | 15 | 66.2 | 99.8 |
| Matrigel-A | 46.6 | 78.4 | 76.5 | 59.7 | 95.7 | 99.6 |
| Matrigel-R | 69.9 | 89.2 | 72.9 | 58.4 | 93.9 | 99.9 |

Figure 11:
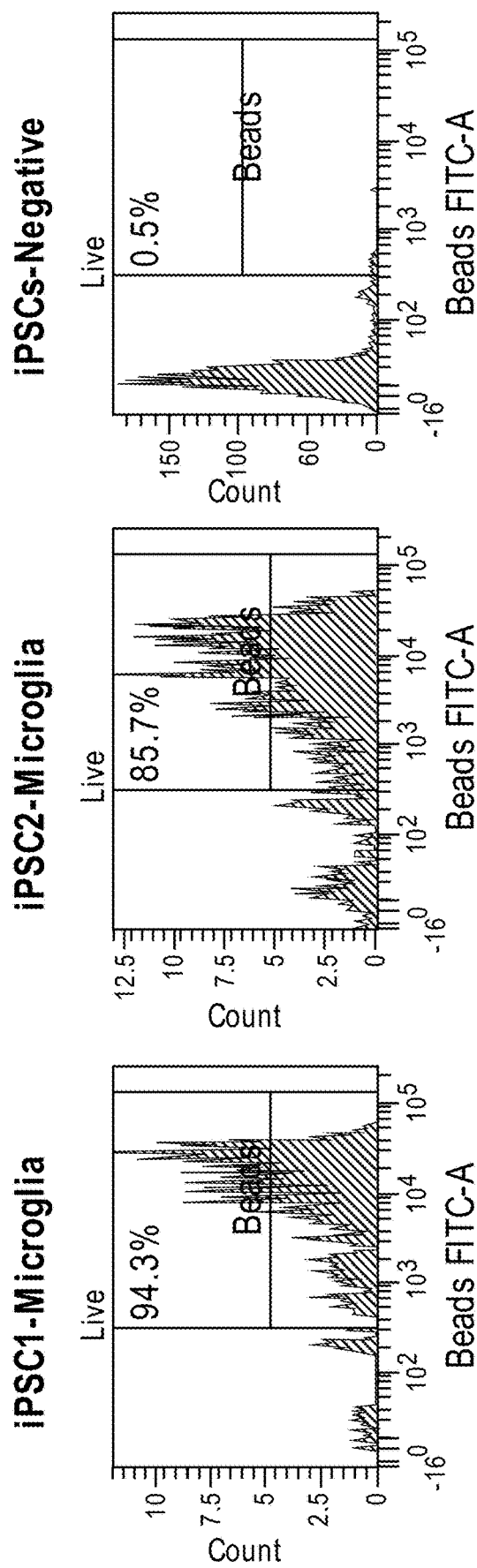
FIG. 11. Data showing that microglial cells differentiated from microglial precursors using the "alternative" or "A" medium described in Example 3 were able to phagocytose carboxylated latex beads. Representative flow cytometry histograms showing that microglial cells differentiated from microglial precursors using the "alternative" or "A" medium described in Example 3 in two independent experiments (iPSC1 and iPSC2) were able to phagocytose YG-labeled carboxylated microspheres. Undifferentiated iPSCs were used as negative control (iPSCs-Negative).
Figure 12:
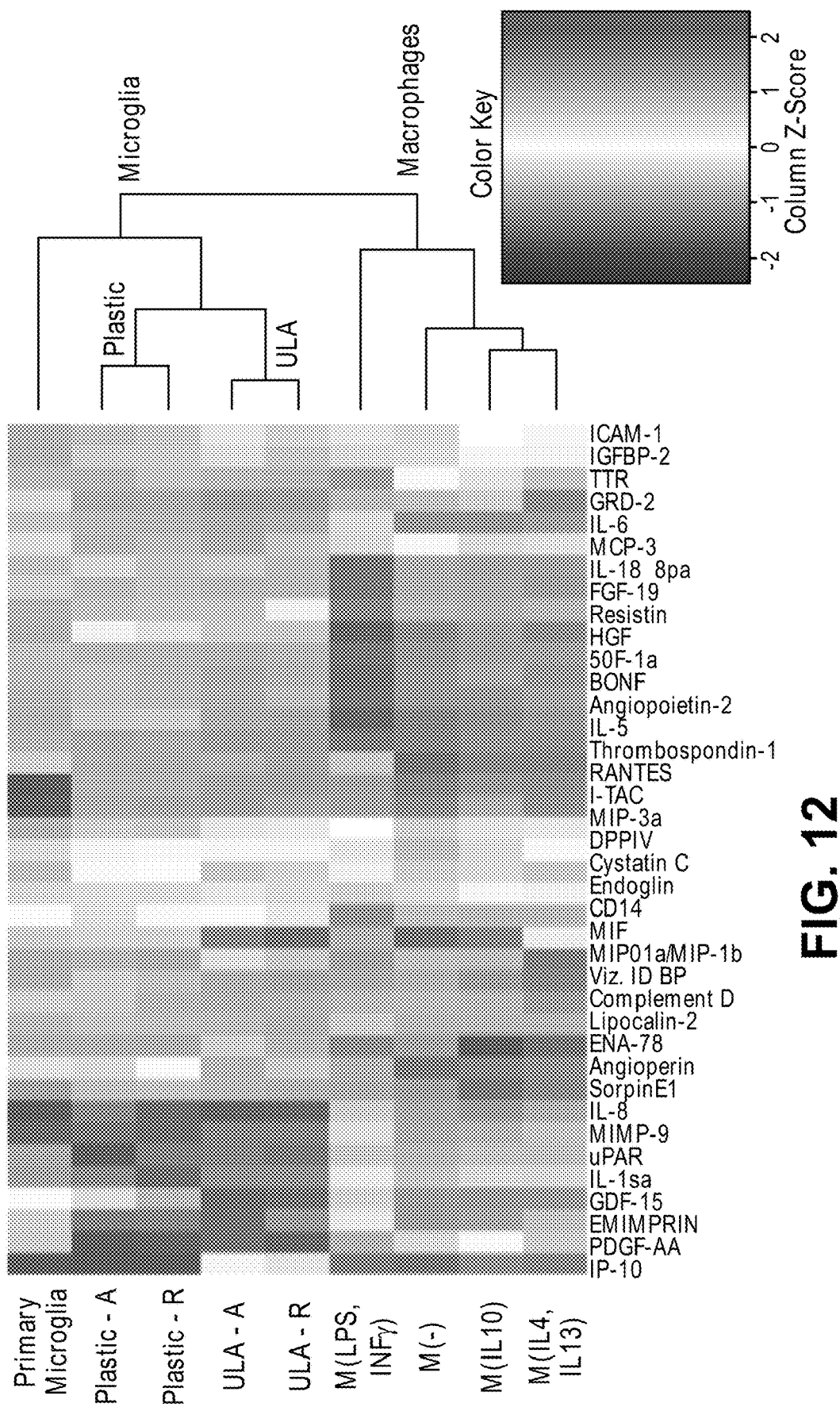
FIG. 12. Heat-map of the released cytokine profiles of iPSC-MG cultured either in the "A" or the "R" medium (as described in Example 3) onto either tissue-culture treated plastic (Plastic) or ultra-low attachment plates (ULA), human primary microglia and peripheral blood-derived macrophages polarized to M(LPS, INFγ), M(IL4, IL13) and M(IL10) or non-polarized M(-). Data show that the cytokine profiles of "A" or "R" microglia are very similar and cluster together with human primary microglia. All microglial cells create a distinct cluster that is separate from macrophages.

As shown in FIG. 11, the microglia cultured in the "A" medium (like those cultured in the "R" medium) were able to phagocytose carboxylated latex beads. As shown in FIG. 12, the cytokines released by microglia cultured either in the "A" or the "R" medium were found to be very similar. It was also found that iPSC-derived microglia cultured on plastic or ultra-low attachment (ULA) plates demonstrated expression profiles that clustered together, and clustered together with human primary microglia, and are separate from peripheral blood-derived macrophages polarized as M(−), M(LPS, IFNγ), M(IL4,IL13) and M(IL10).

The foregoing description of the specific embodiments of the invention will fully reveal the general nature of the invention such that others can, without undue experimentation, apply knowledge that is within the ordinary skill of those in the art to readily modify and/or adapt such specific embodiments for various applications without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

REFERENCE LIST

In addition to the documents cited in other sections of this disclosure, the following references may provide additional context. All of the references cited in this disclosure are hereby incorporated by reference in their entireties. In addition, any manufacturer's instructions or catalogues for any products cited or mentioned herein are incorporated by reference. Documents incorporated by reference into this text, or any teachings therein, can be used in the practice of the present invention. Documents incorporated by reference into this text are not admitted to be prior art.

1. Aarum, J., Sandberg, K., Haeberlein, S. L., and Persson, M. A. (2003). Migration and differentiation of neural precursor cells can be directed by microglia. Proceedings of the National Academy of Sciences of the United States of America 100, 15983-15988.
2. Ajami, B., Bennett, J. L., Krieger, C., Tetzlaff, W., and Rossi, F. M. (2007). Local self-renewal can sustain CNS microglia maintenance and function throughout adult life. Nature neuroscience 10, 1538-1543.
3. Bennett, M. L., Bennett, F. C., Liddelow, S. A., Ajami, B., Zamanian, J. L., Fernhoff, N. B., Mulinyawe, S. B., Bohlen, C. J., Adil, A., Tucker, A., et al. (2016). New tools for studying microglia in the mouse and human CNS. Proceedings of the National Academy of Sciences of the United States of America 113, E1738-1746.
4. Beutner, C., Roy, K., Linnartz, B., Napoli, I., and Neumann, H. (2010). Generation of microglial cells from mouse embryonic stem cells. Nature protocols 5, 1481-1494.
5. Butovsky, O., Jedrychowski, M. P., Moore, C. S., Cialic, R., Lanser, A. J., Gabriely, G., Koeglsperger, T., Dake, B., Wu, P. M., Doykan, C. E., et al. (2014). Identification of a unique TGF-beta-dependent molecular and functional signature in microglia. Nature neuroscience 17, 131-143.
6. Colton, C. A., and Gilbert, D. L. (1987). Production of superoxide anions by a CNS macrophage, the microglia. FEBS letters 223, 284-288.
7. Davalos, D., Grutzendler, J., Yang, G., Kim, J V, Zuo, Y., Jung, S., Littman, D. R., Dustin, M. L., and Gan, W. B. (2005). ATP mediates rapid microglial response to local brain injury in vivo. Nature neuroscience 8, 752-758.
8. Etemad, S., Zamin, R. M., Ruitenberg, M. J., and Filgueira, L. (2012). A novel in vitro human microglia model: characterization of human monocyte-derived microglia. Journal of neuroscience methods 209, 79-89.
9. Fenn, A. M., Henry, C. J., Huang, Y., Dugan, A., and Godbout, J. P. (2012). Lipopolysaccharide-induced interleukin (IL)-4 receptor-alpha expression and corresponding sensitivity to the M2 promoting effects of IL-4 are impaired in microglia of aged mice. Brain, behavior, and immunity 26, 766-777.
10. Ginhoux, F., Greter, M., Leboeuf, M., Nandi, S., See, P., Gokhan, S., Mehler, M. F., Conway, S. J., Ng, L. G., Stanley, E. R., et al. (2010). Fate mapping analysis reveals that adult microglia derive from primitive macrophages. Science 330, 841-845.
11. Hanisch, U. K., and Kettenmann, H. (2007). Microglia: active sensor and versatile effector cells in the normal and pathologic brain. Nature neuroscience 10, 1387-1394.

12. Haynes, S. E., Hollopeter, G., Yang, G., Kurpius, D., Dailey, M. E., Gan, W. B., and Julius, D. (2006). The P2Y12 receptor regulates microglial activation by extracellular nucleotides. Nature neuroscience 9, 1512-1519.
13. Hickman, S. E., Kingery, N. D., Ohsumi, T. K., Borowsky, M. L., Wang, L. C., Means, T. K., and El Khoury, J. (2013). The microglial sensome revealed by direct RNA sequencing. Nature neuroscience 16, 1896-1905.
14. Kierdorf, K., Erny, D., Goldmann, T., Sander, V., Schulz, C., Perdiguero, E. G., Wieghofer, P., Heinrich, A., Riemke, P., Holscher, C., et al. (2013). Microglia emerge from erythromyeloid precursors via Pu.1- and Irf8-dependent pathways. Nature neuroscience 16, 273-280.
15. Luheshi, N. M., Kovacs, K. J., Lopez-Castejon, G., Brough, D., and Denes, A. (2011). Interleukin-1alpha expression precedes IL-1beta after ischemic brain injury and is localised to areas of focal neuronal loss and penumbral tissues. Journal of neuroinflammation 8, 186.
16. Moore, C. S., Ase, A. R., Kinsara, A., Rao, V. T., Michell-Robinson, M., Leong, S. Y., Butovsky, O., Ludwin, S. K., Seguela, P., Bar-Or, A., et al. (2015). P2Y12 expression and function in alternatively activated human microglia. Neurology® neuroimmunology & neuroinflammation 2, e80.
17. Muffat, J., Li, Y., Yuan, B., Mitalipova, M., Omer, A., Corcoran, S., Bakiasi, G., Tsai, L. H., Aubourg, P., Ransohoff, R. M., et al. (2016). Efficient derivation of microglia-like cells from human pluripotent stem cells. Nature medicine 22, 1358-1367.
18. Napoli, I., Kierdorf, K., and Neumann, H. (2009). Microglial precursors derived from mouse embryonic stem cells. Glia 57, 1660-1671.
19. Napoli, I., and Neumann, H. (2009). Microglial clearance function in health and disease. Neuroscience 158, 1030-1038.
20. Nimmerjahn, A. (2012). Two-photon imaging of microglia in the mouse cortex in vivo. Cold Spring Harbor protocols 2012.
21. Nimmerjahn, A., Kirchhoff, F., and Helmchen, F. (2005). Resting microglial cells are highly dynamic surveillants of brain parenchyma in vivo. Science 308, 1314-1318.
22. Ohgidani, M., Kato, T. A., Setoyama, D., Sagata, N., Hashimoto, R., Shigenobu, K., Yoshida, T., Hayakawa, K., Shimokawa, N., Miura, D., et al. (2014). Direct induction of ramified microglia-like cells from human monocytes: dynamic microglial dysfunction in Nasu-Hakola disease. Scientific reports 4, 4957.
23. Paolicelli, R. C., Bolasco, G., Pagani, F., Maggi, L., Scianni, M., Panzanelli, P., Giustetto, M., Ferreira, T. A., Guiducci, E., Dumas, L., et al. (2011). Synaptic pruning by microglia is necessary for normal brain development. Science 333, 1456-1458.
24. Ransohoff, R. M. (2016). How neuroinflammation contributes to neurodegeneration. Science 353, 777-783.
25. Ransohoff, R. M., and Perry, V. H. (2009). Microglial physiology: unique stimuli, specialized responses. Annual review of immunology 27, 119-145.
26. Schulz, C., Gomez Perdiguero, E., Chorro, L., Szabo-Rogers, H., Cagnard, N., Kierdorf, K., Prinz, M., Wu, B., Jacobsen, S. E., Pollard, J. W., et al. (2012). A lineage of myeloid cells independent of Myb and hematopoietic stem cells. Science 336, 86-90.
27. Smith, A. M., and Dragunow, M. (2014). The human side of microglia. Trends in neurosciences 37, 125-135.
28. Sturgeon, C. M., Ditadi, A., Awong, G., Kennedy, M., and Keller, G. (2014). Wnt signaling controls the specification of definitive and primitive hematopoiesis from human pluripotent stem cells. Nature biotechnology 32, 554-561.
29. Tsuchiya, T., Park, K. C., Toyonaga, S., Yamada, S. M., Nakabayashi, H., Nakai, E., Ikawa, N., Furuya, M., Tominaga, A., and Shimizu, K. (2005). Characterization of microglia induced from mouse embryonic stem cells and their migration into the brain parenchyma. Journal of neuroimmunology 160, 210-218.
30. Ueno, M., Fujita, Y., Tanaka, T., Nakamura, Y., Kikuta, J., Ishii, M., and Yamashita, T. (2013). Layer V cortical neurons require microglial support for survival during postnatal development. Nature neuroscience 16, 543-551.
31. Vanhee, S., De Mulder, K., Van Caeneghem, Y., Verstichel, G., Van Roy, N., Menten, B., Velghe, I., Philippe, J., De Bleser, D., Lambrecht, B. N., et al. (2015). In vitro human embryonic stem cell hematopoiesis mimics MYB-independent yolk sac hematopoiesis. Haematologica 100, 157-166.
32. Yanagimachi, M. D., Niwa, A., Tanaka, T., Honda-Ozaki, F., Nishimoto, S., Murata, Y., Yasumi, T., Ito, J., Tomida, S., Oshima, K., et al. (2013). Robust and highly-efficient differentiation of functional monocytic cells from human pluripotent stem cells under serum- and feeder cell-free conditions. PloS one 8, e59243.
33. Zhang, Y., Sloan, S. A., Clarke, L. E., Caneda, C., Plaza, C. A., Blumenthal, P. D., Vogel, H., Steinberg, G. K., Edwards, M. S., Li, G., et al. (2016). Purification and Characterization of Progenitor and Mature Human Astrocytes Reveals Transcriptional and Functional Differences with Mouse. Neuron 89, 37-53.
34. Douvaras, P., Wang, J., Zimmer, M., Hanchuk, S., O'Bara, M. A., Sadiq, S., Sim, F. J., Goldman, J., and Fossati, V. (2014). Efficient generation of myelinating oligodendrocytes from primary progressive multiple sclerosis patients by induced pluripotent stem cells. Stem cell reports 3, 250-259.
35. Enomoto, R., Imamori, M., Seon, A., Yoshida, K., Furue, A., Tsuruda, H., and Lee-Hiraiwa, E. (2013). Proposal for a new evaluation of phagocytosis using different sizes of fluorescent polystyrene microspheres. Advances in Biological Chemistry 03, 556-563.
36. Liao, Y., Smyth, G. K., and Shi, W. (2014). featureCounts: an efficient general purpose program for assigning sequence reads to genomic features. Bioinformatics 30, 923-930.
37. Pallotta, I., Sun, B., Wrona, E. A., and Freytes, D. O. (2015). BMP protein-mediated crosstalk between inflammatory cells and human pluripotent stem cell-derived cardiomyocytes. Journal of tissue engineering and regenerative medicine.
38. Panicker, L. M., Miller, D., Awad, O., Bose, V., Lun, Y., Park, T. S., Zambidis, E. T., Sgambato, J. A., and Feldman, R. A. (2014). Gaucher iPSC-derived macrophages produce elevated levels of inflammatory mediators and serve as a new platform for therapeutic development. Stem cells 32, 2338-2349.
39. Paull, D., Sevilla, A., Zhou, H., Hahn, A. K., Kim, H., Napolitano, C., Tsankov, A., Shang, L., Krumholz, K., Jagadeesan, P., et al. (2015). Automated, high-throughput derivation, characterization and differentiation of induced pluripotent stem cells. Nature Methods 12, 885-892.
40. Robinson, M. D., McCarthy, D. J., and Smyth, G. K. (2010). edgeR: a Bioconductor package for differential expression analysis of digital gene expression data. Bioinformatics 26, 139-140.

41. Woodard, C. M., Campos, B. A., Kuo, S. H., Nirenberg, M. J., Nestor, M W, Zimmer, M., Mosharov, E. V., Sulzer, D., Zhou, H., Paull, D., et al. (2014). iPSC-derived dopamine neurons reveal differences between monozygotic twins discordant for Parkinson's disease. Cell reports 9, 1173-1182.

We claim:

1. A method for generating microglial cells comprising:
   a) culturing pluripotent stem cells in a cell culture medium under conditions that induce myeloid differentiation, leading to the generation of CD14+ and/or CX3CR1+ microglial progenitor cells, wherein culturing comprises contacting the pluripotent stem cells of the cell culture medium with a first composition comprising BMP4 in mTeSR1 media without lithium chloride, GABA, pipecolic acid, bFGF or TGFβ1 and culturing the pluripotent stem cells in the presence of the first composition for approximately 4 days; and
   b) culturing the CD14+ and/or CX3CR1+ microglial progenitor cells in a first microglial differentiation medium comprising IL-34, or comprising IL-34 and GM-CSF, thereby generating microglial cells,
   wherein the CD14+ and/or CX3CR1+ microglial progenitor cells produced in (a) are isolated prior to culturing the CD14+ and/or CX3CR1+ microglial progenitor cells in (b).

2. The method of claim 1, wherein the first composition comprising BMP4 is serum-free.

3. The method of claim 2, further comprising contacting the cell culture medium with a second composition after culturing of the pluripotent stem cells in the presence of the first composition for approximately 4 days, the second composition comprising one or more factors selected from the group consisting of bFGF, SCF, VEGF-A and a combination thereof, in a serum-free hematopoietic cell medium.

4. The method of claim 3, further comprising contacting the cell culture medium with a third composition comprising one or more factors selected from the group consisting of SCF, IL-3, TPO, M-CSF, FLT3 ligand and a combination thereof, in a serum-free hematopoietic cell medium.

5. The method of claim 4, further comprising contacting the cell culture medium with a fourth composition comprising one or more factors selected from the group consisting of M-CSF, FLT3 ligand, GM-CSF and a combination thereof, in a serum-free hematopoietic cell medium.

6. The method of claim 3, comprising contacting the cell culture medium with the second composition for approximately 2 days.

7. The method of claim 4, comprising contacting the cell culture medium with the third composition for approximately 8 days.

8. The method of claim 5, comprising contacting the cell culture medium with the fourth composition for approximately 11 to 36 days.

9. The method of claim 2, wherein the medium suitable for differentiation of pluripotent stem cells does not comprise pluripotency factors.

10. The method of claim 1, wherein the first microglial differentiation medium further comprises GM-CSF.

11. The method of claim 1, wherein the second microglial differentiation medium further comprises one or more factors selected from the group consisting of GM-CSF, NGF-β, CCL2 and a combination thereof.

12. The method of claim 1, wherein the CD14+ and/or CX3CR1+ microglial progenitor cells are cultured in the first or second microglial differentiation medium for approximately 15 days.

13. The method of claim 1, wherein the step of isolating the CD14+ and/or CX3CR1+ microglial progenitor cells comprises contacting the cells with an anti-CD14+ antibody and/or a CX3CR1+ antibody, and separating cells bound by the antibody from cells not bound by the antibody.

14. The method of claim 13, comprising either (i) performing fluorescence activated cell sorting (FACS), or (ii) contacting the cells with magnetic beads that bind directly or indirectly to the antibody, and using a magnet to separate cells bound by the antibody from cells not bound by the antibody.

15. The method of claim 1, comprising collecting cells present in the culture supernatant when media is exchanged, and adding the collected cells back to the cell culture.

16. The method of claim 1, wherein the pluripotent stem cells are induced pluripotent stem (iPS) cells or embryonic stem (ES) cells.

17. The method of claim 1, wherein the pluripotent stem cells are human cells.

* * * * *